(12) United States Patent
Ogura et al.

(10) Patent No.: US 7,250,606 B2
(45) Date of Patent: Jul. 31, 2007

(54) BURIED OBJECT EVALUATING METHOD, UNDERGROUND RESOURCES EVALUATING METHOD, UNDERGROUND WASTE EVALUATING METHOD, UNDERGROUND PRESERVED OBJECT EVALUATING METHOD, STRATUM STRUCTURE EVALUATING METHOD AND BUILDING INTERIOR MONITORING METHOD, ALL USING HARD X-RAYS OR γ-RAYS

(75) Inventors: Kazumasa Ogura, Mihara (JP); Masaki Iijima, Mihara (JP); Yoshikatsu Kuroda, Komaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 205 days.

(21) Appl. No.: 10/946,080

(22) Filed: Sep. 22, 2004

(65) Prior Publication Data
US 2005/0069073 A1    Mar. 31, 2005

(30) Foreign Application Priority Data
Sep. 30, 2003  (JP)  ............................. 2003-342048
Nov. 27, 2003  (JP)  ............................. 2003-398097

(51) Int. Cl.
*G01F 23/00* (2006.01)
*G01V 5/00* (2006.01)
*G01V 5/08* (2006.01)
*G01V 5/10* (2006.01)
*G01N 23/04* (2006.01)

(52) U.S. Cl. .................. 250/358.1; 250/253; 250/256; 250/269.1; 250/269.3; 378/57
(58) Field of Classification Search ............. 250/358.1, 250/253, 256, 269.1, 269.3; 378/57
See application file for complete search history.

(56) References Cited

U.S. PATENT DOCUMENTS

| 3,928,765 A | 12/1975 | Teller |
| 2004/0066890 A1* | 4/2004 | Dalmijn et al. ............... 378/57 |
| 2004/0109532 A1* | 6/2004 | Ford et al. ..................... 378/57 |

\* cited by examiner

*Primary Examiner*—David Porta
*Assistant Examiner*—Mindy Vu
(74) *Attorney, Agent, or Firm*—Wenderoth, Lind & Ponack, L.L.P.

(57) ABSTRACT

As a method for using a hard X-ray sensor that can detect weak hard X-rays or the like with a higher resolution, a method for accurately evaluating natural resources of crude oil, natural gas, etc. existing underground, for example, is provided. A buried object evaluating method includes a detecting step of arranging a radiation detector to be opposed to a hard X-ray source radiating first hard X-rays with a buried object buried in a first substance being interposed between the radiation detector and the radiation source and, by using the radiation detector, detecting second hard X-rays transmitted through the buried object out of the first hard X-rays and third hard X-rays not transmitted through the buried object, and an evaluating step of evaluating the buried object based on a strength of the first hard X-rays and a strength of the second hard X-rays detected by the radiation detector.

26 Claims, 13 Drawing Sheets

(a)          (b)          (c)

BURIED OBJECT EVALUATING METHOD, UNDERGROUND RESOURCES EVALUATING METHOD, UNDERGROUND WASTE EVALUATING METHOD, UNDERGROUND PRESERVED OBJECT EVALUATING METHOD, STRATUM STRUCTURE EVALUATING METHOD AND BUILDING INTERIOR MONITORING METHOD, ALL USING HARD X-RAYS OR γ-RAYS

BACKGROUND OF THE INVENTION

1. Field of the Invention

The present invention relates to a method for evaluating natural resources, etc. including crude oil, natural gas and the like existing underground or for evaluating a stratum structure by using radiation, and for monitoring a building interior by using radiation.

2. Description of the Related Art

A radiation analyzing system by which radiation of hard X-rays, γ-rays or the like is detected so that an image information is generated is actually used in a variety of technological fields. For example, by detecting a radiation field from a certain heavenly body, a physical state or special structure of that heavenly body can be known. Also, by radiating X-rays to the human body or the like and investigating transmission waves thereof, a tomogram image of that human body or the like can be obtained. The radiation analyzing system is otherwise widely used, such as for a nuclear power field (i.e., a vitrification test of radioactive waste, a radiation monitoring device, etc.), a non-destructive inspection field (i.e., a semi-conductor inspection device, etc.), a resources exploring field (an exploration of underground resources, etc.) and the like.

Recently, a new hard X-ray sensor by which weak hard X-rays or the like can be detected with a high resolution has been developed (i.e., Japanese patent applications 2002-261262 and 2003-142670). This hard X-ray sensor is a semi-conductor detector in which CdTe (cadmium telluride) or the like having a relatively large photon blocking power as compared with Si or the like is implemented by a technology called a micro-bump. This sensor has a resolution of about 20 times or more and a detecting time of $\frac{1}{10}$ or less than conventional technology. In this way, this sensor has various advantages so that it has a large possibility to be applied to various technological fields.

Nevertheless, a method for effectively using the above-mentioned hard X-ray sensor for each of the technological fields is not established yet and a prompt development thereof is being desired.

SUMMARY OF THE INVENTION

In view of the above-mentioned circumstances, it is an object of the present invention to provide a method for using the hard X-ray sensor by which weak hard X-rays or the like can be detected with a high resolution, for example, a method for accurately evaluating natural resources of crude oil, natural gas and the like existing underground.

In order to achieve the above-mentioned object, the present invention provides the following.

A first aspect of the present invention is a buried object evaluating method is including a first step of arranging a radiation detector to be opposed to a radiation source radiating a first radiation of hard X-rays or γ-rays with at least a portion of a buried object buried in a first substance being interposed between the radiation detector and the radiation source and, by using the radiation detector, detecting a second radiation transmitted through at least the portion of the buried object out of the first radiation, and a second step of evaluating the buried object based on a strength of the second radiation detected by the radiation detector and a strength of the first radiation.

A second aspect of the present invention includes the buried object evaluating method of the first aspect wherein the second step includes estimating a second substance constituting the buried object based on a strength relative to a propagation distance of the first radiation in each of a plurality of substances and the strength of the second radiation.

A third aspect of the present invention includes the buried object evaluating method of the second aspect wherein the first step includes detecting the second radiation at a plurality of positions different from each other and a third radiation not transmitted through the buried object out of the first radiation and the second step includes estimating a propagation distance of the second radiation in the buried object based on the strength relative to the propagation distance of the first radiation and the strength of the second radiation and quantitatively evaluating the buried object based on at least one of the propagation distance of the second radiation and a detection distribution representing a distribution of the second radiation detected at the plurality of positions different from each other.

A fourth aspect of the present invention is an underground resources evaluating method which include a first step of arranging a radiation detector to be opposed to a radiation source radiating a first radiation of hard X-rays or γ-rays with at least a portion of underground resources buried underground being interposed between the radiation detector and the radiation source and, by using the radiation detector, detecting a second radiation transmitted through at least the portion of the underground resources out of the first radiation, and a second step of evaluating the underground resources based on a strength of the second radiation detected by the radiation detector and a strength of the first radiation.

A fifth aspect of the present invention includes the underground resources evaluating method of the fourth aspect wherein the underground resources are crude oil and the second step includes estimating an existence of an oil field based on a strength relative to a propagation distance of the first radiation in the crude oil and the strength of the second radiation.

A sixth aspect of the present invention includes the underground resources evaluating method of the fourth aspect wherein the underground resources are natural gas and the second step includes estimating an existence of a natural gas field based on a strength relative to a propagation distance of the first radiation in the natural gas and the strength of the second radiation.

A seventh aspect of the present invention includes the underground resources evaluating method of the fourth aspect wherein the underground resources are coal and the second step includes estimating an existence of a coal field based on a strength relative to a propagation distance of the first radiation in the coal and the strength of the second radiation.

An eighth aspect of the present invention includes the underground resources evaluating method of the fourth aspect wherein the underground resources are a predetermined metal and the second step includes estimating an existence of an ore deposit of the predetermined metal based on a strength relative to a propagation distance of the first radiation in the predetermined metal and the strength of the second radiation.

A ninth aspect of the present invention includes the underground resources evaluating method of any one of the fourth to the eighth aspects wherein the first step includes detecting the second radiation at a plurality of positions different from each other and a third radiation not transmitted through the underground resources out of the first radiation and the second step includes estimating a propagation distance of the second radiation in the underground resources based on a strength relative to a propagation distance of the first radiation and the strength of the second radiation and quantitatively evaluating the underground resources based on at least one of the propagation distance of the second radiation and a detection distribution representing a distribution of the second radiation detected at the plurality of positions different from each other.

A tenth aspect of the present invention is an underground waste evaluating method including a first step of arranging a radiation detector to be opposed to a radiation source radiating a first radiation of hard X-rays or γ-rays with at least a portion of waste disposed underground being interposed between the radiation detector and the radiation source and, by using the radiation detector, detecting a second radiation transmitted through at least the portion of the waste out of the first radiation, and a second step of evaluating the waste based on a strength of the second radiation detected by the radiation detector and a strength of the first radiation.

An eleventh aspect of the present invention includes the underground waste evaluating method of the tenth aspect wherein the waste is an injected carbon dioxide and the second step includes estimating an existence of the injected carbon dioxide based on a strength relative to a propagation distance of the first radiation in the injected carbon dioxide and the strength of the second radiation.

A twelfth aspect of the present invention includes the underground waste evaluating method of the tenth or eleventh aspect wherein the first step includes detecting the second radiation at a plurality of positions different from each other and a third radiation not transmitted through the waste out of the first radiation and the second step includes estimating a propagation distance of the second radiation in the waste based on a strength relative to a propagation distance of the first radiation and the strength of the second radiation and quantitatively evaluating the waste based on at least one of the propagation distance of the second radiation and a detection distribution representing a distribution of the second radiation detected at the plurality of positions different from each other.

A thirteenth aspect of the present invention is an underground preserved object evaluating method including a first step of arranging a radiation detector to be opposed to a radiation source radiating a first radiation of hard X-rays or γ-rays with at least a portion of a preserved object preserved underground being interposed between the radiation detector and the radiation source and, by using the radiation detector, detecting a second radiation transmitted through at least the portion of the preserved object out of the first radiation, and a second step of evaluating the preserved object based on a strength of the second radiation detected by the radiation detector and a strength of the first radiation.

A fourteenth aspect of the present invention includes the underground preserved object evaluating method of the thirteenth aspect wherein the preserved object is natural gas and the second step includes estimating an existence of the natural gas based on a strength relative to a propagation distance of the first radiation in the natural gas and the strength of the second radiation.

A fifteenth aspect of the present invention includes the underground preserved object evaluating method of the thirteenth or fourteenth aspect wherein the first step includes detecting the second radiation at a plurality of positions different from each other and a third radiation not transmitted through the preserved object out of the first radiation and the second step includes estimating a propagation distance of the second radiation in the preserved object based on a strength relative to a propagation distance of the first radiation and the strength of the second radiation and quantitatively evaluating the preserved object based on at least one of the propagation distance of the second radiation and a detection distribution representing a distribution of the second radiation detected at the plurality of positions different from each other.

A sixteenth aspect of the present invention is an underground buried object evaluating method including a first step of arranging a radiation detector to be opposed to a radiation source radiating a first radiation of hard X-rays or γ-rays with at least a portion of a buried object buried underground being interposed between the radiation detector and the radiation source and, by using the radiation detector, detecting a second radiation transmitted through at least the portion of the buried object out of the first radiation, and a second step of evaluating the buried object based on a strength of the second radiation detected by the radiation detector and a strength of the first radiation.

A seventeenth aspect of the present invention, the underground buried object evaluating method of the sixteenth aspect wherein the buried object is a mine, nuclear weapon or other military weapons or other buried objects and the second step includes estimating an existence of the mine, nuclear weapon or other military weapons or other buried objects based on a strength relative to a propagation distance of the first radiation in the mine, nuclear weapon or other military weapons or other buried objects and the strength of the second radiation.

A eighteenth aspect of the present invention includes the underground buried object evaluating method of the sixteenth or seventeenth aspect wherein the first step includes detecting the second radiation at a plurality of positions different from each other and a third radiation not transmitted through the buried object out of the first radiation and the second step includes estimating a propagation distance of the second radiation in the buried object based on a strength relative to a propagation distance of the first radiation and the strength of the second radiation and quantitatively evaluating the buried object based on at least one of the propagation distance of the second radiation and a detection distribution representing a distribution of the second radiation detected at the plurality of positions different from each other.

A nineteenth aspect of the present invention is a volcanic activity evaluating method including a first step of arranging a radiation detector to be opposed to a radiation source radiating a first radiation of hard X-rays or γ-rays with at least a portion of a volcano being interposed between the radiation detector and the radiation source and, by using the radiation detector, detecting a second radiation transmitted through at least the portion of the volcano out of the first radiation, and a second step of evaluating an activity of the volcano based on a strength of the second radiation detected by the radiation detector and a strength of the first radiation.

A twentieth aspect of the present invention includes the volcanic activity evaluating method of the nineteenth aspect wherein the first step includes detecting the second radiation at a plurality of positions different from each other and a third radiation not transmitted through magma of the volcano out of the first radiation and the second step includes estimating a propagation distance of the second radiation in the magma based on a strength relative to a propagation distance of the first radiation and the strength of the second radiation and quantitatively evaluating the activity of the volcano based on the propagation distance of the second radiation and a detection distribution representing a distribution of the second radiation detected at the plurality of positions different from each other.

A twenty-first aspect of the present invention is an object interior evaluating method including a first step of arranging a test system comprising a radiation detector opposed to a radiation source radiating a first radiation of hard X-rays or γ-rays with at least a portion of a test object being interposed between the radiation detector and the radiation source and, while moving the test system along an external shape of the test object, detecting a second radiation transmitted through the test object out of the first radiation, and a second step of evaluating a physical state of an interior of the test object based on a strength of the second radiation detected by the radiation detector and a strength of the first radiation.

A twenty-second aspect of the present invention includes the object interior evaluating method of the twenty-first aspect wherein the test object is any one of a concrete building, an iron frame building, a stone building, a piping and a liquid reservoir and the second step includes estimating an existence of a crack or foreign matter in the test object based on at least one of a strength relative to a propagation distance of the first radiation in each of a plurality of substances and the strength of the second radiation.

A twenty-third aspect of the present invention includes the object interior evaluating method of the twenty-first aspect wherein the test object is any one of a piping and a fluid reservoir and the second step includes estimating a flow state of fluid in the test object based on at least one of a strength relative to a propagation distance of the first radiation in each of a plurality of substances and the strength of the second radiation.

A twenty-fourth aspect of the present invention is a buried object evaluating method including a first step of radiating a neutron beam to a buried object buried in a first substance to thereby cause a second substance constituting the buried object and a neutron to interact with each other so that a radiation of hard X-rays or γ-rays is released from the second substance, a second step of, by using a radiation detector, detecting the radiation released from the second substance, and a third step of evaluating the buried object based on a strength of the radiation detected by the radiation detector.

A twenty-fifth aspect of the preset invention includes the buried object evaluating method of the twenty-fourth aspect wherein the third step includes estimating the second substance constituting the buried object based on a spectrum of the radiation detected by the radiation detector.

A twenty-sixth aspect of the present invention includes the buried object evaluating method of the twenty-fourth aspect wherein the third step includes quantitatively evaluating the buried object based on a generation quantity of the radiation detected by the radiation detector.

A twenty-seventh aspect of the present invention is an underground resources evaluating method including a first step of radiating a neutron beam to underground resources buried underground to thereby cause a first substance constituting the underground resources and a neutron to interact with each other so that a radiation of hard X-rays or γ-rays is released from the first substance, a second step of, by using a radiation detector, detecting the radiation released from the first substance, and a third step of evaluating the underground resources based on a strength of the radiation detected by the radiation detector.

A twenty-eighth aspect of the present invention includes the underground resources evaluating method of the twenty-seventh aspect wherein the third step includes estimating the first substance based on a spectrum of the radiation detected by the radiation detector and thereby evaluating an existence of the underground resources.

A twenty-ninth aspect of the present invention includes the underground resources evaluating method of the twenty-eighth aspect wherein the underground resources are crude oil and the third step includes estimating liquid hydrocarbon for the first substance and thereby evaluating that the underground resources are an oil field.

A thirtieth aspect of the present invention includes the underground resources evaluating method of the twenty-eighth aspect wherein the underground resources are natural gas and the third step includes estimating gas hydrocarbon for the first substance and thereby evaluating that the underground resources are a natural gas field.

A thirty-first aspect of the present invention includes the underground resources evaluating method of the twenty-eighth aspect wherein the underground resources are coal and the third step includes estimating carbon for the first substance and thereby evaluating that the underground resources are a coal field.

A thirty-second aspect of the present invention includes the underground resources evaluating method of the twenty-eighth aspect wherein the underground resources are a predetermined metal and the third step includes estimating the predetermined metal for the first substance and thereby evaluating that the underground resources are a metal ore deposit.

A thirty-third aspect of the present invention including the underground resources evaluating method of any one of the twenty-seventh to the thirty-second aspects is characterized in that the third step includes quantitatively evaluating the underground resources based on a generation quantity of the radiation detected by the radiation detector.

As a thirty-fourth aspect of the present invention is an underground waste evaluating method including a first step of radiating a neutron beam to waste disposed underground to thereby cause a first substance constituting the waste and a neutron to interact with each other so that a radiation of hard X-rays or γ-rays is released from the first substance, a second step of, by using a radiation detector, detecting the radiation released from the first substance, and a third step of evaluating the waste based on a strength of the radiation detected by the radiation detector.

A thirty-fifth aspect of the present invention includes the underground waste evaluating method of the thirty-fourth aspect wherein the third step includes estimating the first substance based on a spectrum of the radiation detected by the radiation detector and thereby evaluating an existence of the waste.

A thirty-sixth aspect of the present invention includes the underground waste evaluating method of the thirty-fourth or thirty-fifth aspect wherein the waste is an injected carbon dioxide.

A thirty-seventh aspect of the present invention includes the underground waste evaluating method of any one of the thirty-fourth to the thirty-sixth aspects is characterized in that the third step includes quantitatively evaluating the waste based on a generation quantity of the radiation detected by the radiation detector.

A thirty-eighth aspect of the present invention is an underground preserved object evaluating method including a first step of radiating a neutron beam to a preserved object preserved underground to thereby cause a second substance constituting the preserved object and a neutron to interact with each other so that a radiation of hard X-rays or γ-rays is released from the first substance, a second step of, by using a radiation detector, detecting the radiation released from the first substance, and a third step of evaluating the preserved object based on a strength of the radiation detected by the radiation detector.

A thirty-ninth aspect of the present invention including the underground preserved object evaluating method of the thirty-eighth aspect wherein the third step includes estimating the first substance based on a spectrum of the radiation detected by the radiation detector.

A fortieth aspect of the present invention includes the underground preserved object evaluating method of the thirty-eighth or thirty-ninth aspect wherein the preserved object is natural gas and the third step includes estimating gas hydrocarbon for the first substance and thereby evaluating that the preserved object is a natural gas field.

A forty-first aspect of the present invention includes the underground preserved object evaluating method of any one of the thirty-eighth to the fortieth aspects wherein the third step includes quantitatively evaluating the preserved object based on a generation quantity of the radiation detected by the radiation detector.

A forty-second aspect of the present invention is a flow state evaluating method including a first step of radiating a neutron beam to fluid reserved in a vessel to thereby cause the fluid and a neutron to interact with each other so that a radiation of hard X-rays or γ-rays is released from the fluid, a second step of, by using a radiation detector, detecting the radiation released from the fluid, and a third step of evaluating a flow state of the fluid based on a strength of the radiation detected by the radiation detector.

A forty-third aspect of the present invention includes the flow state evaluating method of the forty-second aspect wherein the third step includes estimating a density of the fluid based on a spectrum of the radiation detected by the radiation detector and thereby evaluating the flow state of the fluid.

A forty-fourth aspect of the present invention includes the flow state evaluating method of the forty-second or forty-third aspect wherein the third step includes quantitatively evaluating the flow state of the fluid based on a generation quantity of the radiation detected by the radiation detector.

A forty-fifth aspect of the present invention is a flow state evaluating method including a first step of radiating a neutron beam to an area including a flow path of volcanic magma to thereby cause a substance existing in the area and a neutron to interact with each other so that a radiation of hard X-rays or γ-rays is released from the substance, a second step of, by using a radiation detector, detecting the radiation released from the substance, and a third step of evaluating a flow state of the volcanic magma based on a strength of the radiation detected by the radiation detector.

A forty-sixth aspect of the present invention includes the flow state evaluating method of the forty-fifth aspect wherein the third step includes estimating a density of the substance based on a spectrum of the radiation detected by the radiation detector and thereby evaluating the flow state of the volcanic magma.

A forty-seventh aspect of the present invention includes the flow state evaluating method of the forty-fifth aspect wherein the third step includes quantitatively evaluating the flow state of the volcanic magma based on a generation quantity of the radiation detected by the radiation detector.

A forty-eighth aspect of the present invention is a stratum structure evaluating method including a first step of arranging a radiation detector to be opposed to a radiation source radiating a first radiation of hard X-rays or γ-rays with a stratum being interposed between the radiation detector and the radiation source and, by using the radiation detector, detecting a second radiation transmitted through the stratum out of the first radiation, and a second step of evaluating a fault or active fault existing in the stratum based on a strength of the second radiation detected by the radiation detector and a strength of the first radiation.

A forty-ninth aspect of the present invention includes the stratum structure evaluating method of the forty-eighth aspect wherein the first step includes detecting the second radiation at a plurality of positions different from each other and a third radiation not transmitted through the fault or active fault out of the first radiation and the second step includes estimating a propagation distance of the second radiation in the fault or active fault based on a strength relative to a propagation distance of the first radiation and the strength of the second radiation and quantitatively evaluating the fault or active fault based on the propagation distance of the second radiation and a detection distribution representing a distribution of the second radiation detected at the plurality of positions different from each other.

A fiftieth aspect of the present invention is a building interior monitoring method including a first step of arranging a radiation detector to be opposed to a radiation source radiating a first radiation of hard X-rays or γ-rays with a predetermined space in a building being interposed between the radiation detector and the radiation source and, by using the radiation detector, detecting a second radiation transmitted through the predetermined space out of the first radiation, and a second step of evaluating a human being or thing existing in the predetermined space based on a strength of the second radiation detected by the radiation detector and a strength of the first radiation and thereby monitoring an interior of the building.

A fifty-first aspect of the present invention includes the building interior monitoring method of the fiftieth aspect wherein the first step includes detecting the second radiation at a plurality of positions different from each other and a third radiation not transmitted through the human being or thing out of the first radiation and the second step includes estimating a propagation distance of the second radiation in the human being or thing based on a strength relative to a propagation distance of the first radiation and the strength of the second radiation and quantitatively evaluating the human being or thing based on the propagation distance of the second radiation and a detection distribution representing a distribution of the second radiation detected at the plurality of positions different from each other.

According to the present invention of any one of the above-mentioned aspects, there is provided a method for effectively using a hard X-ray sensor that can accurately detect weak hard X-rays or the like with a high resolution. Thereby, various methods can be realized, for example, for evaluating natural resources including crude oil, natural gas and the like or for evaluating a buried object, underground waste, underground preserved object and stratum structure as well as for monitoring a building interior.

DETAILED DESCRIPTION OF THE INVENTION

Figure 1:
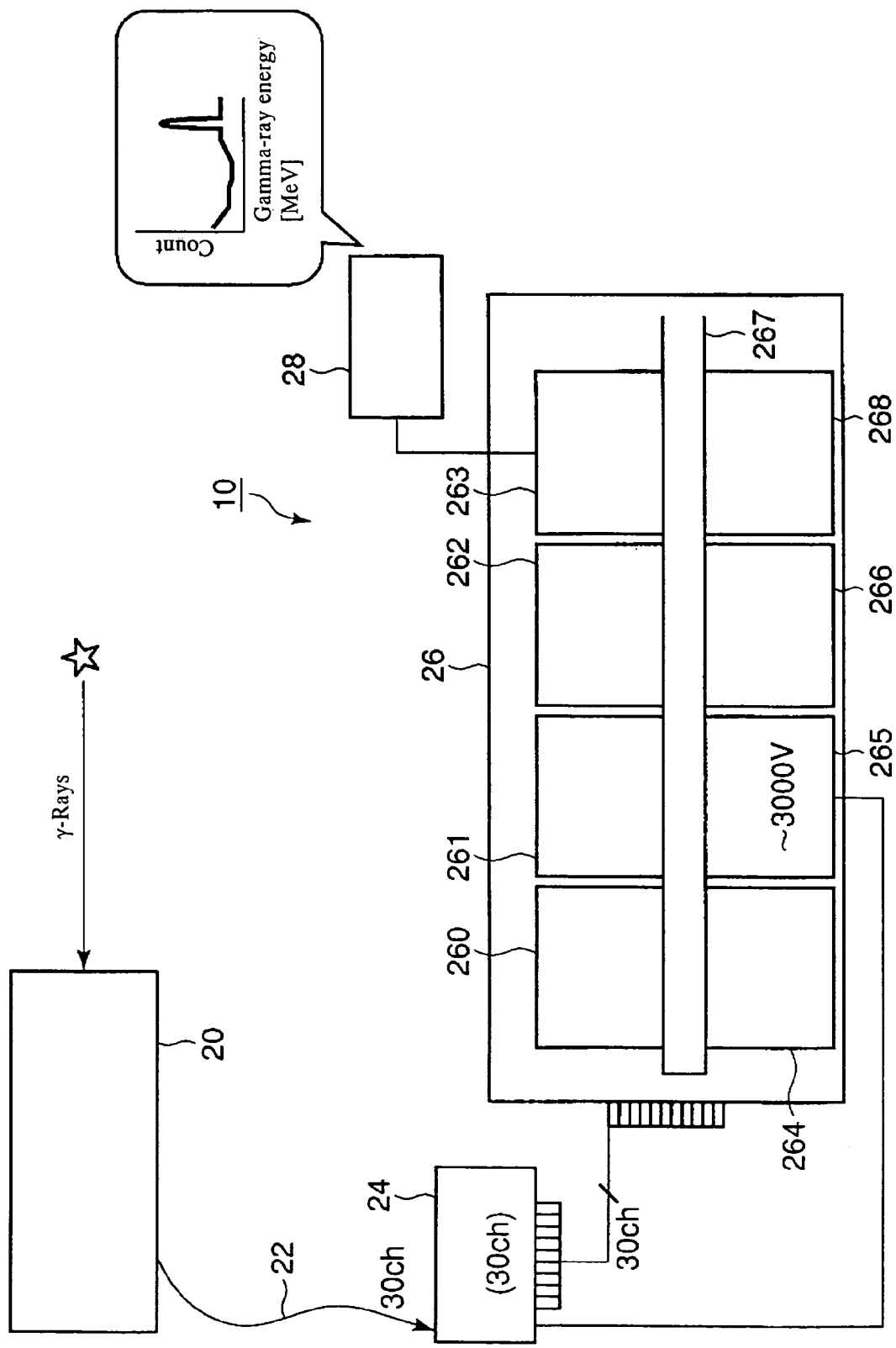
FIG. 1 is a block diagram showing a construction of a radiation analyzing system 10 used in embodiments according to the present invention.

Herebelow, embodiments according to the present invention will be described with reference to the appended drawings. In the description and illustration below, it is to be noted that the constructional elements having substantially the same function and construction are designated with the same reference numerals and repeated description thereof will be omitted except where needed.

(Radiation Analyzing System)

A construction of a radiation analyzing system used in the embodiments according to the present invention will be first described. FIG. 1 is a block diagram showing a construction of a radiation analyzing system 10 used in the embodiments according to the present invention. As shown there, the radiation analyzing system 10 comprises a radiation detector 20, a signal processing part 24, a detected gamma-rays analyzing unit 26 and a computer 28.

The radiation detector 20 detects hard X-rays or γ-rays and comprises a detector plate as a detecting face, as will be described later. If a direction and position of a radiation source are to be detected, a plurality of the detector plates are laminated in the direction of incidence of the radiation so that the respective detector plates are independently movable along this direction of incidence of the radiation. Details of the radiation detector 20 will be described later.

The signal processing part 24 amplifies a detected signal detected by the radiation detector 20 so as to prevent mixing of noises and deterioration of S/N (signal-to-noise) ratio. Also, the signal processing part 24 performs such signal processing as sampling of the detected signal, a further amplification thereof, a generation of a trigger signal, holding of samples, etc.

The detected gamma-rays analyzing unit 26 comprises an A/D converting part 260, a discriminator 261, a trigger signal generating and bit pattern obtaining part 262, a system bus PC translator 263, an MCA (multi-channel analyzer) 264, a high voltage electric source 265, a wave shaping part 266, a system bus 267 and a memory 268.

The A/D converting part 260 converts an inputted analog signal to a digital signal.

The discriminator 261 takes out an original signal wave from a frequency-modulated or phase-modulated signal wave.

The trigger signal generating and bit pattern obtaining part 262 obtains a bit pattern of detected gamma-rays based on the signal wave selected by the discriminator 261. The detected information of the gamma-rays obtained by the trigger signal generating and bit pattern obtaining part 262 is transmitted to the computer 28 for a measurement of a distance and direction to a gamma-ray source, as will be described below. It is to be noted that the construction may be made such that the generation of the trigger signal and obtaining of the bit pattern are carried out by the computer 28.

The system bus PC translator 263 is a transmitter transmitting various signals from the system bus 267 to the computer 28.

The MCA 264 performs a histogram processing of a signal value of the digital signal converted by the A/D converting part 260.

The high voltage electric source 265 generates a high voltage to be charged to an electrode of each of the detector plates of the radiation detector 20. In each of the detector plates having its electrode supplied with the high voltage from the high voltage electric source 265, if the detector plate is a semi-conductor, an electron and positive hole are generated by the incidence of the gamma-rays. Also, if the detector plate is a scintillator, a light in the area of a visible radiation to an ultraviolet radiation is generated by the incidence of the gamma-rays.

The wave shaping part 266 converts a wave shape of an input pulse to a predetermined wave shape on and along an amplitude axis or time axis.

The system bus 267 is a circuit for transmitting and receiving various signals between each of devices in the detected gamma-rays analyzing unit 26.

The memory 268 stores a bit pattern of the gamma-rays obtained by the trigger signal generating and bit pattern obtaining part 262.

The computer 28 is a work station having a function of numerical processing, image processing, etc., or a personal computer or the like. The computer 28 performs a measurement of an energy count distribution of the detected gamma-rays as shown in FIG. 1, based on the detected gamma-ray information of the radiation detector 20 received from the detected gamma-rays analyzing unit 26, or performs processing of a quantitative analysis, substance analysis or the like, as will be described later, corresponding to the degree of attenuation of the measured gamma-rays.

It is to be noted that if the detected gamma-rays analyzing unit 26 is constructed to be given with a function of further numerical processing, image processing, etc., the quantitative analysis or the like, to be described later, can be performed by the detected gamma-rays analyzing unit 26 so constructed.

(Radiation Detector)

Next, a construction of the radiation detector 20 will be described in detail.

Figure 2:
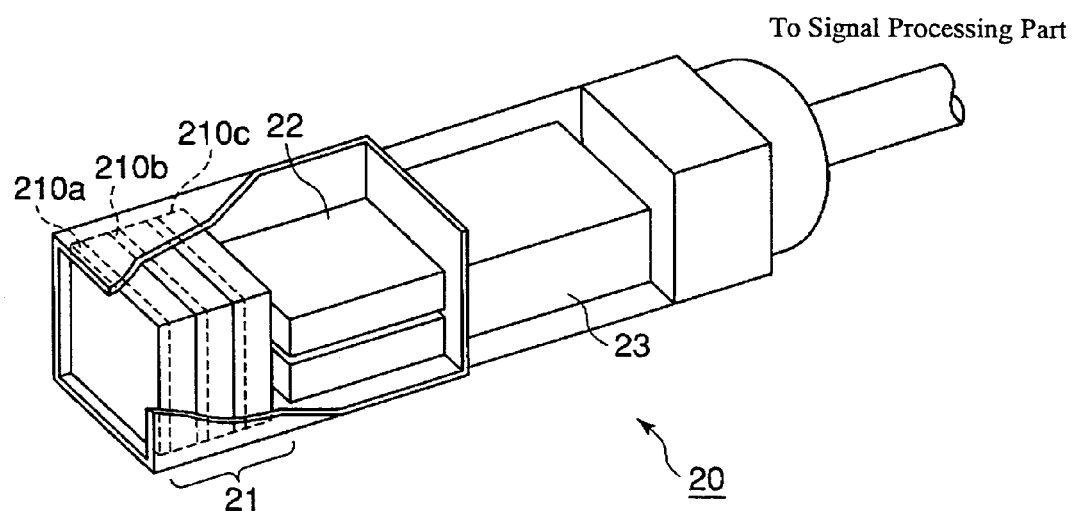
FIG. 2 is a partially cut-away perspective view of a radiation detector 20.

FIG. 2 is a partially cut-away perspective view of the radiation detector 20. As shown there, the radiation detector 20 comprises a sensor part 21, a pre-amplification part 22 and a sampling amplification part 23.

The sensor part 21 is constructed by a laminate of image sensors 210*a*, 210*b* and 210*c*, as shown in FIG. 2. A signal detected by each of the image sensors can be independently read out. If the sensor part 21 performs a quantitative analysis and substance analysis of an evaluation object, to be described later, the outermost image sensor 210*a* is used in principle. But if a direction and position of a hard X-ray source are to be evaluated, for example, a plurality of the image sensors are used at the same time. It is to be noted that while the example of the sensor part 21 shown in FIG. 2 uses the laminate of three image sensors, the number of sensors to be laminated is not limited to three but may be an arbitrary number.

The image sensors 210*a*, 210*b* and 210*c* are semi-conductor detectors using a semi-conductor of CdTe, CdZnTe (cadmium zinc telluride) or the like. Hereinbelow, for the purpose of concreteness of the description, an example of using the CdTe will be described. CdTe is a compound semi-conductor comprising Cd (cadmium) and Te (tellurium) and its energy gap is about 1.47 eV at room temperature.

Figure 3:
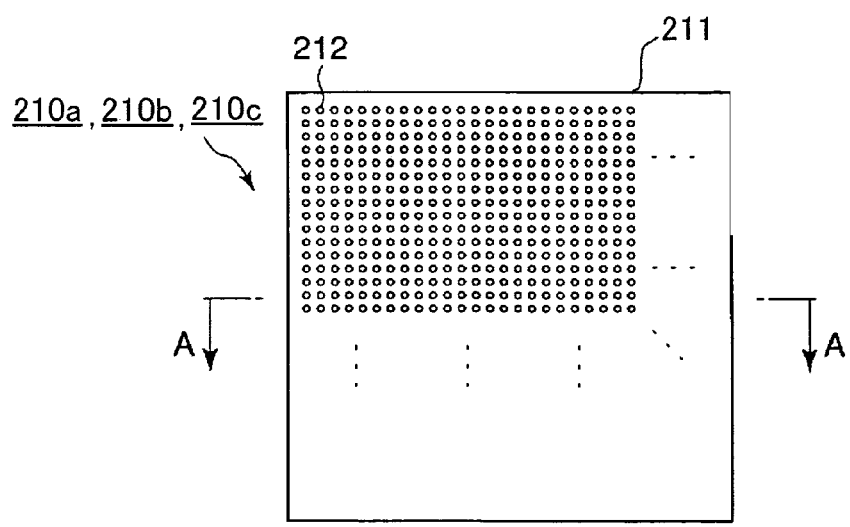
FIG. 3 is a plan view of a detecting face of image sensors 210a, 210b and 210c.
Figure 4:
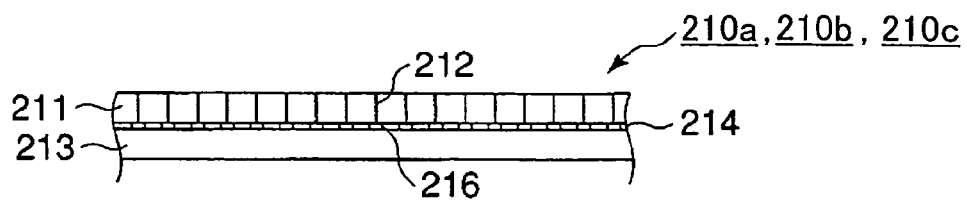
FIG. 4 is a cross-sectional view of the detecting face of the image sensors 210a, 210b and 210c.

FIG. 3 is a plan view of the detecting face of each of the image sensors 210*a*, 210*b* and 210*c*. FIG. 4 is a cross-sectional view of the detecting face taken on line A-A of FIG. 3. As shown in FIGS. 3 and 4, each of the image sensors 210*a*, 210*b* and 210*c* comprises a semi-conductor plate 211, an IC substrate 213 and a connecting layer 214. The semi-conductor plate 211 is made of CdTe and has a plurality of first electrodes 212 of hole type bored therein with a predetermined pitch being maintained between each of the first electrodes 212. The IC substrate 213 has an IC implemented thereon for amplifying a detected signal. The connecting layer 214 functions to connect the semi-conductor plate 211 and the IC substrate 213 to each other.

The first electrodes 212 of the hole type are formed such that a plurality of holes are bored in the semi-conductor plate 211 by a drill having an outer diameter of about 100 to 200 μm with a predetermined pitch (i.e., 50 μm) being maintained between each of the holes, and the holes are applied with metallizing of Pt, Hg, Au, InTe, Al or the like. Each of the first electrodes 212 has its one end provided with a second electrode 216 (pad) that functions as an electric connector between the first electrode 212 and an electric wiring leading means to be described below (see FIGS. 5 and 6).

It is to be noted that, generally, as CdTe or CdZnTe is a substance that is brittle and noxious to the human body, the plurality of holes are formed by a special process. Also, in a predetermined mode of use, the first electrode 212 is separated into an anode and a cathode and the separated anode and cathode and a part of the CdTe form a sensor element.

Figure 5:
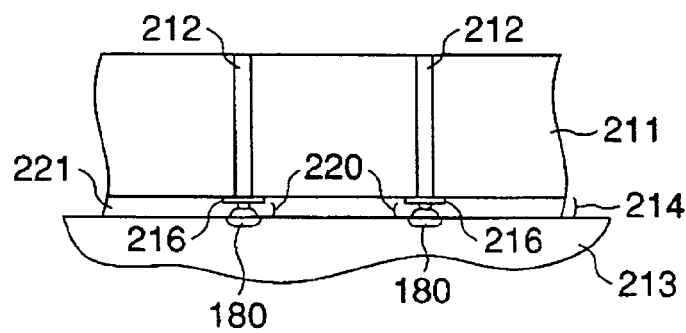
FIG. 5 is an enlarged view of first electrodes 212 and the surroundings thereof of the image sensor of FIG. 4.
Figure 6:
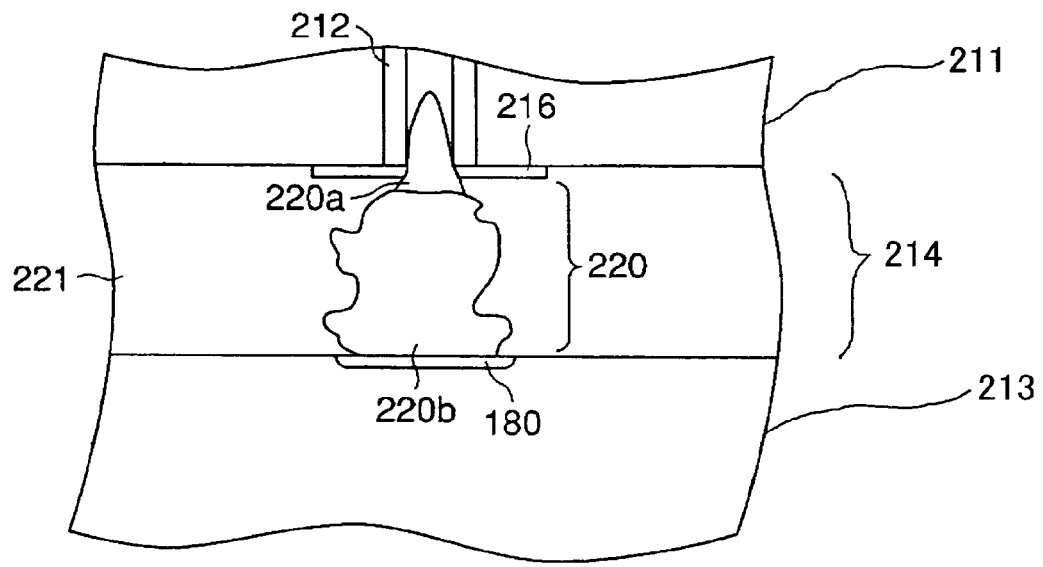
FIG. 6 is a schematic view for explaining an electric connection between one of the first electrodes 212 and an IC substrate 213.

Next, the connecting layer 214 interposed between the semi-conductor plate 211 and the IC substrate 213 will be described with reference to FIGS. 4 to 6. FIG. 5 is an enlarged view showing the first electrodes 212 and the surroundings thereof of the image sensor of FIG. 4. FIG. 6 is a schematic view for explaining an electric connection between one of the first electrodes 212 and the IC substrate 213. As shown in FIGS. 5 and 6, the connecting layer 214 comprises a stud bump connecting portion 220 and an insulating layer 221. The stud bump connecting portion 220 functions to perform an FC (flip chip) implementation of the semi-conductor plate 211 onto the IC substrate 213.

The stud bump connecting portion 220 is formed on an FC pad 180 formed on the IC substrate 213 and comprises an Au stud bump 220*a* made of Au or the like and an indium layer 220*b* formed at a terminal end of the Au stud bump 220*a*. The Au stud bump 220*a* is formed by one stage of a projection-shaped bump arranged on the FC pad 180 or by a laminate of two stages or more of the projection-shaped bumps arranged on the FC pad 180. This Au stud bump 220*a* functions to effect an electric supply between the sensor element and the IC, to reduce a leak current between the sensor elements (especially, if the number of layers is increased to two stages, three stages or more, the leak current can be largely reduced) and to absorb a connecting error in performing the FC implementation. Therefore, the material thereof is preferably a relatively soft metal having a good conductivity and in the present embodiment, Au is used. But other materials having the same or similar function may also be used.

The indium layer 220*b* comprises a thin film layer provided at the terminal end of the Au stud bump 220*a* and a portion projecting into the first electrode 212. The indium layer 220b, while in the manufacturing process thereof, is formed in a tapered shape having a predetermined height and, in the FC implementation, is fitted to the second electrode 216 by pressure welding. The indium layer 220b functions to effect a secure electric supply between the sensor element and the IC and to provide a predetermined height that is needed for the FC implementation, as will be described later. As for the material thereof, as the CdTe element is used in the present embodiment, a solder material having a melting point of 100° C. or less is preferable. That is, for example, bismuth other than indium can be used.

(Buried Object Evaluating Method)

Next, a method for qualitatively and/or quantitatively evaluating an object buried in a substance by using the above-mentioned sensor system will be described. This evaluating method mainly includes two types, that is, a transmission wave detecting type and a reaction spectrum detecting type. The principle of each of them will be described below. It is to be noted, however, that a substance specifying method and a quantitative evaluating method of each of the types are only examples and no limitation to these examples is intended.

(Transmission Wave Detecting Type)

The principle of the transmission wave detecting type will be described. This method focuses on the attenuation of hard X-rays based on a density difference of propagation mediums (e.g., the attenuation of hard X-rays and the like that have been propagated in an object buried in a substance and the attenuation of hard X-rays and the like that have not been propagated in the object buried in the substance).

Figure 7:
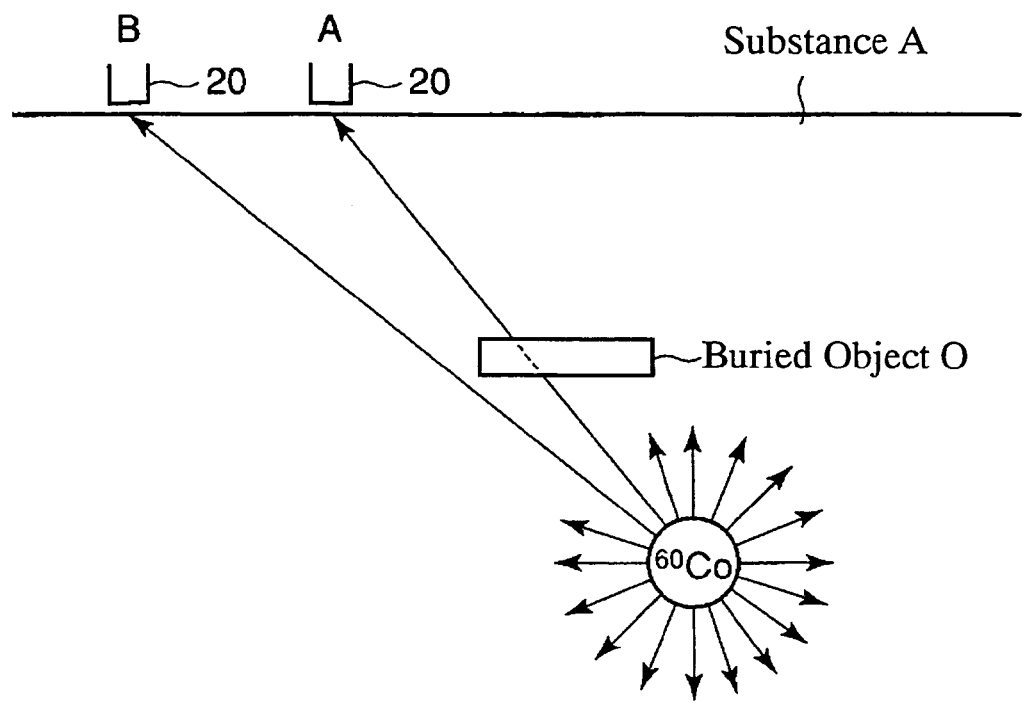
FIG. 7 is a schematic view for explaining the principle of a transmission wave detecting type evaluating method.

FIG. 7 is a schematic view for explaining the principle of the transmission wave detecting type evaluating method. As shown there, an object O exists in a substance A. Also, a substance that radiates hard X-rays, cobalt 60 ($^{60}$Co) for example, is arranged in the substance A. By this arrangement, as the hard X-rays have a strong transmission ability, the transmission wave that has been transmitted (propagated) through the substance A or the object O can be detected at a surface of the substance A.

In this state, the hard X-rays are measured at position A and position B and the strengths thereof are compared. That is, the strength of the hard X-rays detected at the position A has an influence of being transmitted through the object O (an influence caused by the density difference between the object O and the substance A).

That is, the strength of the hard X-rays measured at the position B approximately equals a value estimated by the transmission factor of the substance A (=1–the attenuation factor) and the transmission distance thereof. However, as the X-rays measured at the position A have been transmitted through the object O that has a density different from the substance A, the strength thereof deviates by the degree of the influence given by the object O from the value estimated by the transmission factor of the substance A and the transmission distance thereof. Thus, if a deviation of the hard X-ray strength caused by the object O is measured, or more concretely, if a hard X-ray strength deviating by the influence of the object O having a density different from the substance A from an estimated strength of the hard X-rays at the position A if the hard X-rays would have been transmitted only through the substance A is measured, it can be so evaluated that the object O exists on a path connecting the cobalt 60 and the position A.

Also, based on the difference between the estimated strength of the hard X-rays at the position A if the hard X-rays would have been transmitted only through the substance A and the actually measured hard X-ray strength at the position A, it is possible to specify the substance constituting the object O and to quantitatively evaluate the object O.

That is, where the transmission factor of the substance A (=1–the attenuation factor) is f1, the transmission distance of hard X-rays to the position A is x1, the transmission factor of the object O (=1–the attenuation factor) is f2, the transmission distance of hard X-rays to the position A is x2 and the initial value of hard X-rays of the cobalt 60 is Io, the hard X-ray strength $I_A$ at the position A can be generally formulated as the following equation (1):

$$I_A = I_o \exp[-f1 x1] \cdot \exp[-f2 x2] \quad (1)$$

Here, if the distance between the cobalt 60 and the position A is L, as L=x1+x2, the following equation can be formed:

$$I_A = I_o \exp[-f1 L] \cdot \exp[-x2(f2-f1)] \quad (2)$$

In the above equation (2), Ioexp [−f1L] is known and $I_A$ can be obtained by the measurement. Hence, value V of exp [−x2 (f2−f1)] can be obtained. Comparisons are made between this value V and various values V'=exp [−x (f−f1)] calculated in advance for each of the transmission distance x with respect to respective transmission factors f of plural substances and a substance and transmission distance that substantially coincide with the comparison result are specified. Thereby, the substance constituting the object O can be evaluated.

Also, by measuring the influence of the object O not only at the position A but also at a plurality of positions on the surface of the substance A, a two dimensional distribution showing the existence of the object O can be grasped. By this distribution and the transmission distance obtained as mentioned above, an approximate volume of the object O can be obtained.

(Reaction Spectrum Detecting Type)

The principle of the reaction spectrum detecting type will be described next. In this method, spectrum of γ-rays radiated from an atomic nucleus or the like of an atom included in a buried object is measured to thereby obtain an information on the structure of the atomic nucleus or other expertise information on that atom and based on such information, evaluation of the buried object is carried out.

Figure 8:
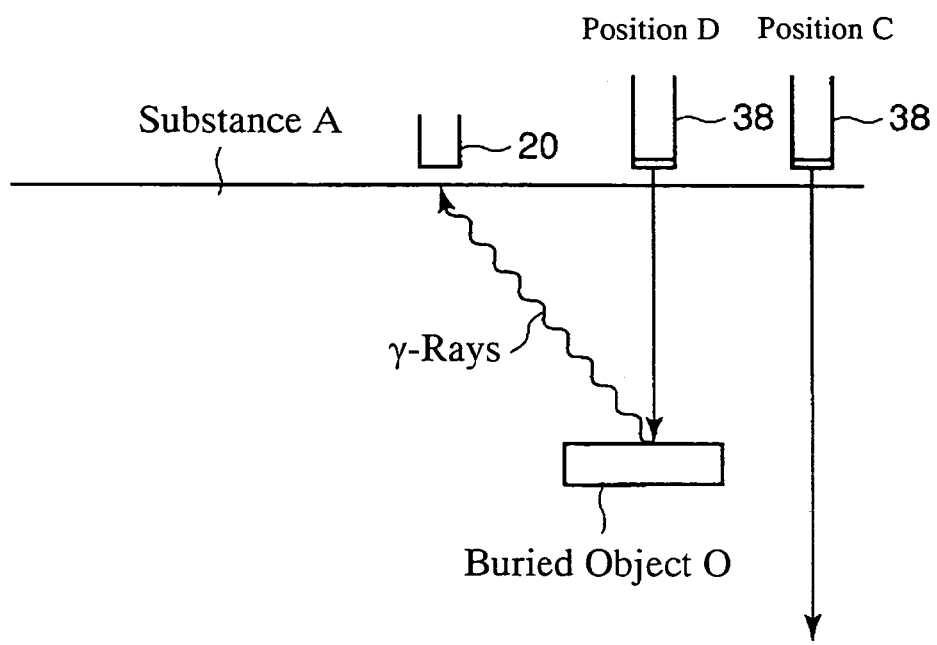
FIG. 8 is a schematic view for explaining the principle of a reaction spectrum detecting type evaluating method.

FIG. 8 is a schematic view for explaining the principle of the reaction spectrum detecting type evaluating method. As shown therein, a case where an object O exists in a substance A is considered. In this state, a neutron is radiated into the substance A from a neutron generator gun 38. In this case, the radiated neutron is transmitted in the substance A or reacts on (interacts with) a specific element (C, N, O, etc. for example). The illustration of FIG. 8 shows an example where the neutron radiated from position C is transmitted in the substance A and the neutron radiated from position D reacts on a specific element constituting the object O.

Upon occurrence of such reaction, there arises a transition of the energy level of a particle (i.e., a nucleon of a predetermined atom) that has interacted with the neutron and hard X-rays (γ-rays) having a spectrum proper to the element are generated. This spectrum is measured by a radiation detector 20 to be analyzed and thereby the existence of a substance including the specific atom can be evaluated. Also, the strength (frequency of the generation) of the hard X-rays including a predetermined spectrum is measured and thereby the atom corresponding to that spectrum can be quantitatively evaluated.

(Underground Resources Evaluating Method)

Next, a method for evaluating underground resources by using the above-mentioned sensor system will be described, wherein embodiments are shown corresponding to the kind of resources as the evaluation object.

(Oil Field Evaluating Method 1)

Figure 9:
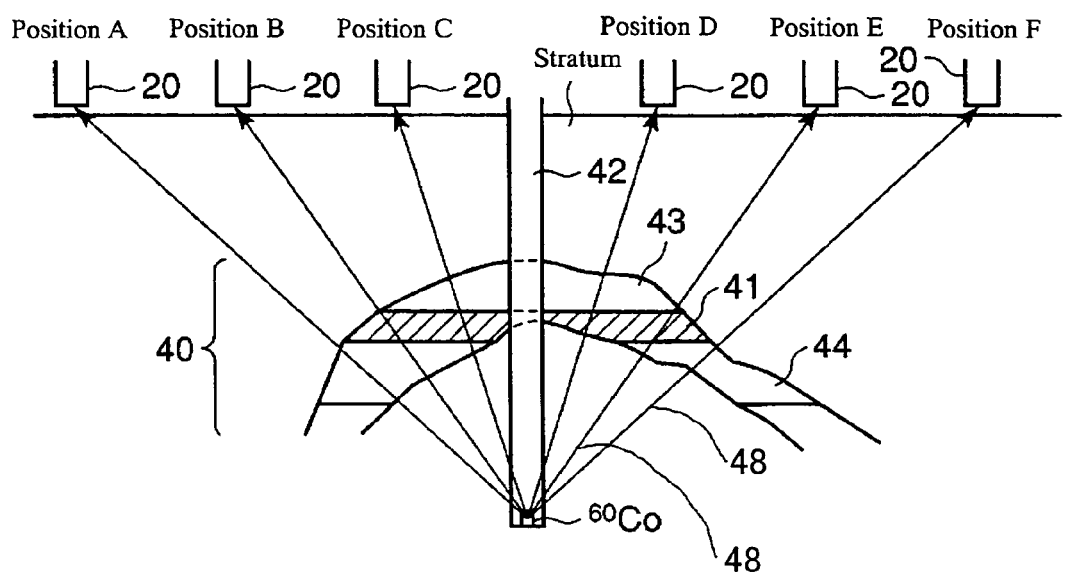
FIG. 9 is a schematic view for explaining an oil field evaluating method of the transmission wave detecting type.

FIG. 9 is a schematic view for explaining an oil field evaluating method of the transmission wave detecting type. As shown there, a case where a reservoir rock 40 exists in an underground stratum is considered. The reservoir rock 40 comprises an oil reservoir 41 in which oil is reserved, a gas reservoir 43 in which gas of hydrocarbon (natural gas) is reserved and a water reservoir 44. Herein, a topographic structure in which the above-mentioned reservoir rock 40 exists is referred to as "an oil field".

In the environment in which such oil field exists, a well 42 is bored passing through at least a portion of the oil reservoir 41 and a hard X-rays generating source, cobalt 60 for example, is arranged therein. The cobalt 60 arranged in the well 42 radiates hard X-rays 48 to be measured by radiation detectors 20 at a plurality of positions (position A to position F in the illustration of FIG. 9). At least at the position B to the position E, the hard X-ray strength estimated at each of the positions if the environment would have no oil field (e.g., if the environment has the stratum only) is influenced by the existence of the oil field, that is, by the density change due to the propagation mediums. Thus, the existence of the oil field can be evaluated.

Also, the hard X-rays measured at the position A and the position F are not propagated through the oil reservoir 41 that has a high density and, as compared with the hard X-rays measured at the position B to the position E, have less attenuation so that the strength thereof becomes higher by that degree. Thereby, an approximate two dimensional or three dimensional distribution of the oil reservoir 41 can be evaluated and as the result thereof, not only the existence of the oil field but also the oil reserved in the oil field can be quantitatively evaluated.

(Oil Field Evaluating Method 2)

Figure 10:
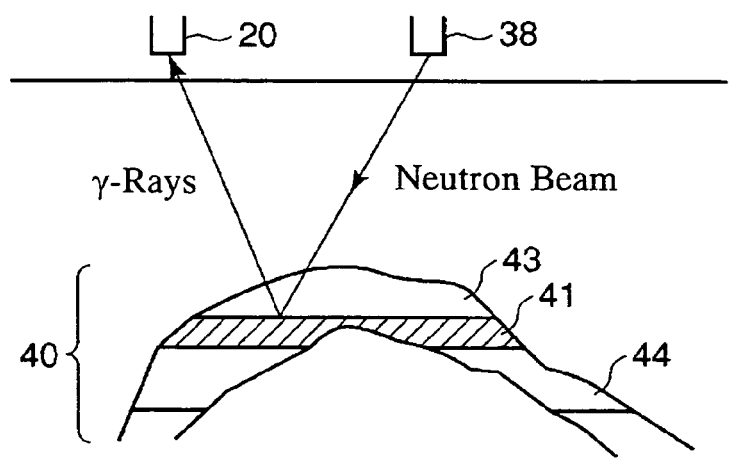
FIG. 10 is a schematic view for explaining an oil field evaluating method of the reaction spectrum detecting type.

FIG. 10 is a schematic view for explaining an oil field evaluating method of the reaction spectrum detecting type. As shown there, a neutron generator gun 38 is arranged on the ground surface and neutron is radiated into the ground by the neutron generator gun 38. The radiated neutron reacts on (interacts with) an element constituting the oil (hydrocarbon, etc.) included in the oil reservoir 41, for example C (more in detail, C and H in the oil and/or gas, H and O in the water). Upon occurrence of such reaction, there arises a transition of the energy level of a particle (i.e., a nucleon) that has interacted with the neutron and hard X-rays (γ-rays) are released. The spectrum of the hard X-rays is measured by the radiation detector 20 to be analyzed and thereby the existence of a substance including the specific atom can be evaluated. Also, by measuring the strength (frequency of the generation) of the hard X-rays including a predetermined spectrum, the oil reserved in the oil field can be quantitatively evaluated.

According to each of the oil field evaluating methods described above, as compared with the prior art method, a large cost reduction can be realized. Herebelow, concrete contents thereof will be described in comparison with the prior art method.

Figure 11:
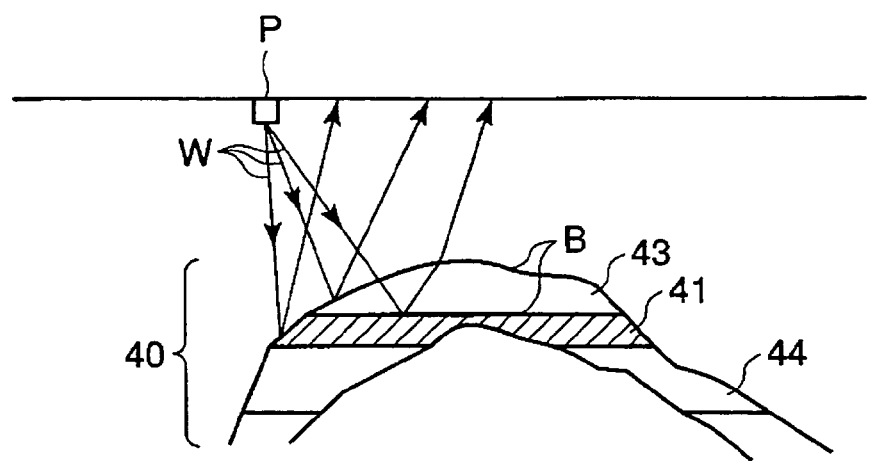
FIG. 11 is a schematic view for explaining a prior art evaluating method for evaluating an existence of an oil field (seismic prospecting method).

FIG. 11 is a schematic view for explaining a prior art oil field evaluating method (seismic prospecting method). At position P shown there, earthquakes, for example, are artificially generated so that a seismic wave (elastic wave) W is generated. In this oscillating wave, there arises a phenomenon of refraction or reflection at a boundary of the strata having different physical properties. The seismic prospecting method is a technology to observe these phenomena and evaluate the structure of underground resources and is mainly classified to a refraction method and a reflection method. In the refraction method, the stratum structure is evaluated by making use of a refraction wave propagated along a stratum boundary B corresponding to the difference of the index of refraction. Also, in the reflection method, the time until the oscillating wave reflects at the stratum boundary B and comes back to the ground surface corresponding to the difference of the index of refraction is measured and the seismic intensity to the reflecting surface is evaluated.

In such seismic prospecting method in the prior art, there are problems as mentioned below, for example:

Firstly, an evaluation of the underground resources cannot be done on the spot. That is, as the object of this method is non-homogenous underground rocks or minerals, large noises are included in the reflecting wave, etc. and hence the underground structure cannot be known on the spot of measurement. Thus, usually, the oscillating ground movement within a predetermined time after the generation of the elastic wave is recorded on a recording medium on the spot and afterwards, in the environment having sufficient research facilities, etc., data processing is carried out. Therefore, a large work and time are needed for the evaluation of the underground resources.

Secondly, a quantitative evaluation cannot be done. That is, in the seismic prospecting method, while an evaluation of whether resources exist or not is possible, a quantitative evaluation of a distribution area, etc. of the resources is impossible.

Thirdly, a large cost is required. That is, from the viewpoint of accuracy, while an approximate underground structure is first grasped by the seismic prospecting method, it is then necessary that a plurality of wells are bored for confirming the existence of the oil field and the quantity of oil. Thus, in some cases, the cost may amount to as large as several hundred million yen to several billion yen.

According to the respective evaluating methods of the embodiments of the present invention, all of the above-mentioned problems can be solved. That is, the radiation detected by the radiation detector 20 is speedily and automatically analyzed by the detected gamma-rays analyzing unit 26 and the computer 28. Hence, a quick and accurate evaluation of resources, especially a quantitative evaluation, becomes possible on the spot. Also, according to the method of the present invention, the number of wells required can be reduced as compared with the seismic prospecting method and as the result thereof, an extremely large cost reduction can be realized.

(Evaluating Method of Natural Gas Field, Coal Field, Metal Ore Deposit, Etc.)

The above-described oil field evaluating method of the transmission wave detecting type as well as oil field evaluating method of the reaction spectrum detecting type can also be applied to the evaluation of a natural gas field, coal field, metal ore deposit, etc. as they are by changing the substance data, such as a transmission factor, etc. and the same effect can be obtained.

(Underground Waste Evaluating Method 1)

Next, a method for evaluating a waste disposed underground by using the above-mentioned sensor system will be described, wherein an example where the waste is atmospheric carbon dioxide that is injected underground as a recent technology under development for preventing the global warming is used.

Figure 12:
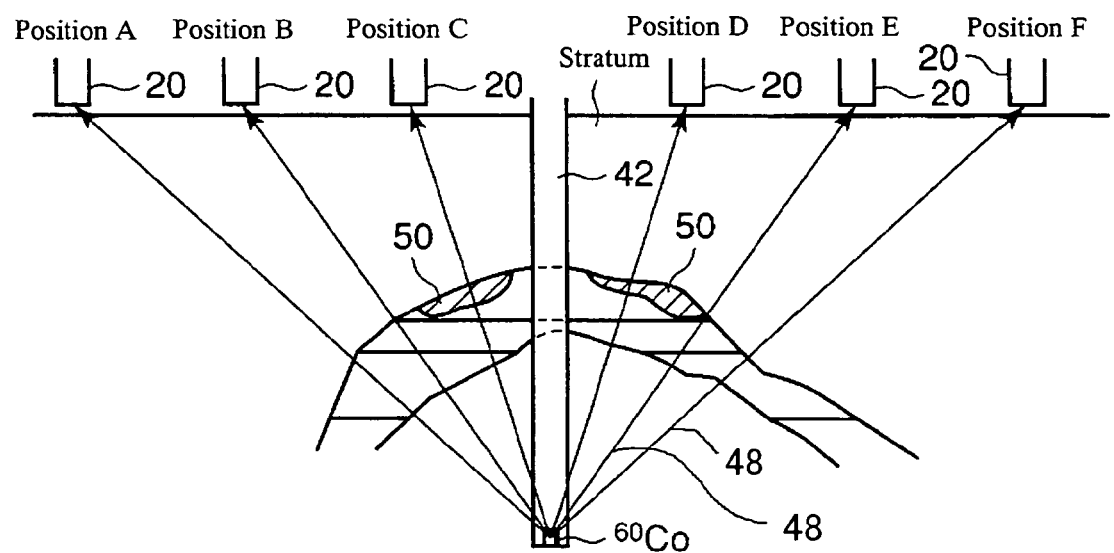
FIG. 12 is a schematic view for explaining an underground waste evaluating method of the transmission wave detecting type.

FIG. 12 is a schematic view for explaining an underground waste evaluating method of the transmission wave detecting type. As shown there, carbon dioxide 50 as a waste is injected into a stratum boundary portion, for example.

In such environment, like in the evaluation of the oil field, a well 42 is bored and a hard X-rays generating source, cobalt 60 for example, is arranged therein. The cobalt 60 arranged in the well 42 radiates hard X-rays 48 to be measured by radiation detectors 20 at a plurality of positions. At least at positions C, D and E, the hard X-ray strength estimated at each of the positions if the environment would have no such injected carbon dioxide 50 (e.g., if the environment has the stratum only) is influenced by the existence of the injected carbon dioxide 50, that is, by the density change due to the propagation mediums. Thus, the existence of the injected carbon dioxide can be evaluated.

Also, the hard X-rays measured at positions A, B and F are not propagated through the injected carbon dioxide that has a density different from the stratum and, as compared with the hard X-rays measured at the positions C, D and E, have less attenuation so that the strength thereof changes by that degree. Thereby, an approximate two dimensional or three dimensional distribution of the injected carbon dioxide can be evaluated and as the result thereof, not only the existence of the injected carbon dioxide 50 but also the injected carbon dioxide 50 so preserved can be quantitatively evaluated.

(Underground Waste Evaluating Method 2)

Figure 13:
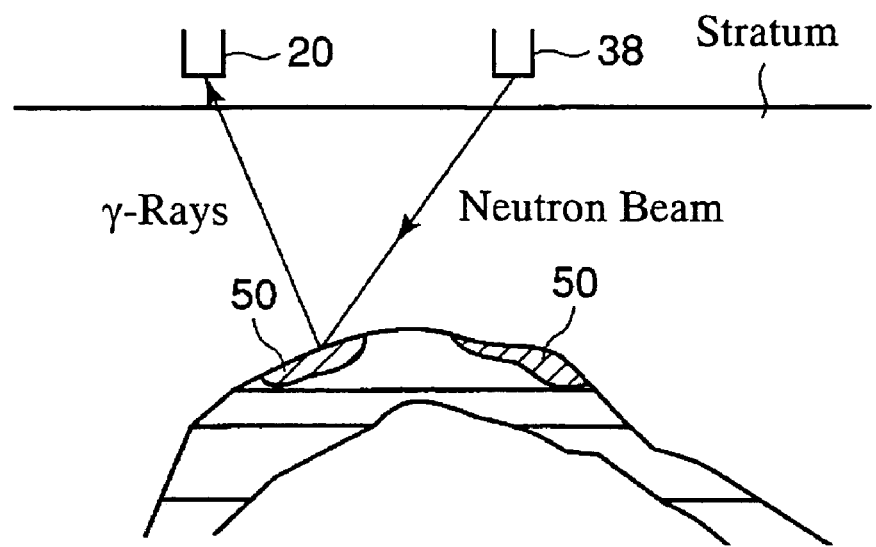
FIG. 13 is a schematic view for explaining an underground waste evaluating method of the reaction spectrum detecting type.

FIG. 13 is a schematic view for explaining an underground waste evaluating method of the reaction spectrum detecting type. As shown there, neutron is radiated into the ground by the neutron generator gun 38. The radiated neutron reacts on (interacts with) the injected carbon dioxide or a nucleon or the like constituting the injected carbon dioxide. Upon occurrence of such reaction, there arises a transition of the energy level of a particle that has interacted with the neutron and hard X-rays ($\gamma$-rays) are radiated. The spectrum of the hard X-rays is measured by the radiation detector 20 to be analyzed and thereby the existence of the injected carbon dioxide 50 can be evaluated. Also, by measuring the strength (frequency of the generation) of the hard X-rays including a predetermined spectrum, the injected carbon dioxide 50 can be quantitatively evaluated.

(Underground Preserved Object Evaluating Method)

The above-described underground waste evaluating method of the transmission wave detecting type as well as underground waste evaluating method of the reaction spectrum detecting type can also be applied to the evaluation of an underground preserved object of natural gas, etc. as they are by changing the substance data, such as a transmission factor, etc. and the same effect can be obtained.

(Non-Destructive Test: Evaluating Method of Crack, Etc.)

Next, an example where the above-mentioned sensor system is applied to a non-destructive test of a large size building or the like will be described. In this non-destructive test, the evaluating method of the transmission wave detecting type is used.

Figure 14:
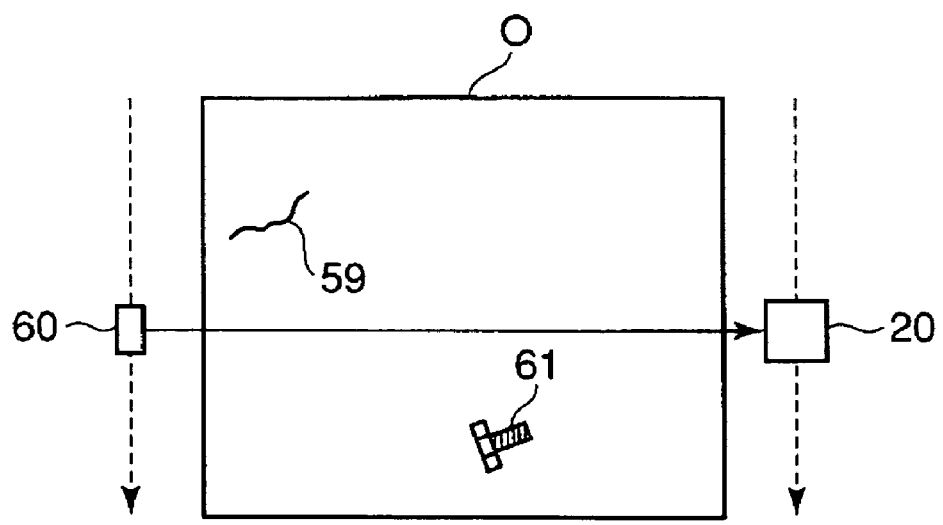
FIG. 14 is a schematic view for explaining a non-destructive test method of a large size building, etc. according to the present sensor system.

For example, as shown in FIG. 14, a case where a crack 59 exists in an object O is considered. A hard X-ray source 60 is provided on one side of the object O and a sensor 20 is arranged on the other side being opposed to the hard X-ray source 60 with the object O being interposed therebetween.

In the setting so arranged, while the hard X-ray source 60 and the sensor 20 are being opposed to each other, they are moved so as to cover all areas of both sides of the object O, as shown by broken lines in FIG. 14, and the strength of the transmitted hard X-rays is measured at each of position. In this case, there appears an influence caused by the density difference between the strength measured by the sensor 20 of the hard X-rays transmitted through the crack 59 and the strength measured by the sensor 20 of the hard X-rays not transmitted through the crack 59.

That is, the strength of the hard X-rays not transmitted through the crack 59 approximately equals a value estimated by the transmission factor (=1−the attenuation factor) of a substance constituting the object O and the transmission distance thereof. However, as the crack 59 has a density different from the substance constituting the object O, the strength of the hard X-rays transmitted through the crack 59 deviates by the degree of the influence given by the crack 59 from the value estimated by the transmission factor of the substance constituting the object O and the transmission distance thereof. Thus, if a deviation of the hard X-ray strength caused by the crack 59 is measured, or more concretely, if a hard X-ray strength deviating by the influence of the crack 59 having a density different from the substance constituting the object O from an estimated strength of the hard X-rays if the hard X-rays would have been transmitted only through the substance constituting the object O is measured, it can be so evaluated that the crack 59 exists on a path connecting the hard X-ray source 60 and the sensor 20.

Also, based on the differential value between the estimated strength of the hard X-rays if the hard X-rays would have been transmitted only through the substance constituting the object O and the actually measured hard X-ray strength, it is possible to specify a physical state within the object O or other substances existing in the object O and also to quantitatively evaluate them.

That is, for example, supposing that a bolt 61 exists in the object O, the strength of the hard X-rays transmitted through the bolt 61 deviates from the strength of the hard X-rays not transmitted through the bolt 61. Hence, by obtaining a distribution of positions where the hard X-rays having the deviation of the strength are measured, the size of the bolt 61 can be quantitatively evaluated.

Also, the deviation value of the above-mentioned X-ray strength depends on a substance (or a metal) constituting the bolt 61. Hence, by comparing the deviation value using a table showing the relation between the transmission distance (thickness) and the hard X-ray strength, prepared in advance for each of substances, it is possible to specify a raw material of the bolt 61 existing in the object O and to quantitatively evaluate the thickness thereof.

Next, concrete examples of non-destructive tests using the above-mentioned sensor system will be described for each of buildings included therein as an evaluation object. It is to be noted that, in each of the examples, while the hard X-ray source and the sensor are arranged being opposed to each other, it is necessary that at least one of them is moved along an outer wall, etc. of the building. The mode of this movement is arbitrary but, from the viewpoint of preventing a human body exposure, etc., it is preferable to use an unmanned means using a robot, remote control or the like.

(Non-Destructive Test of Dam)

Figure 15:
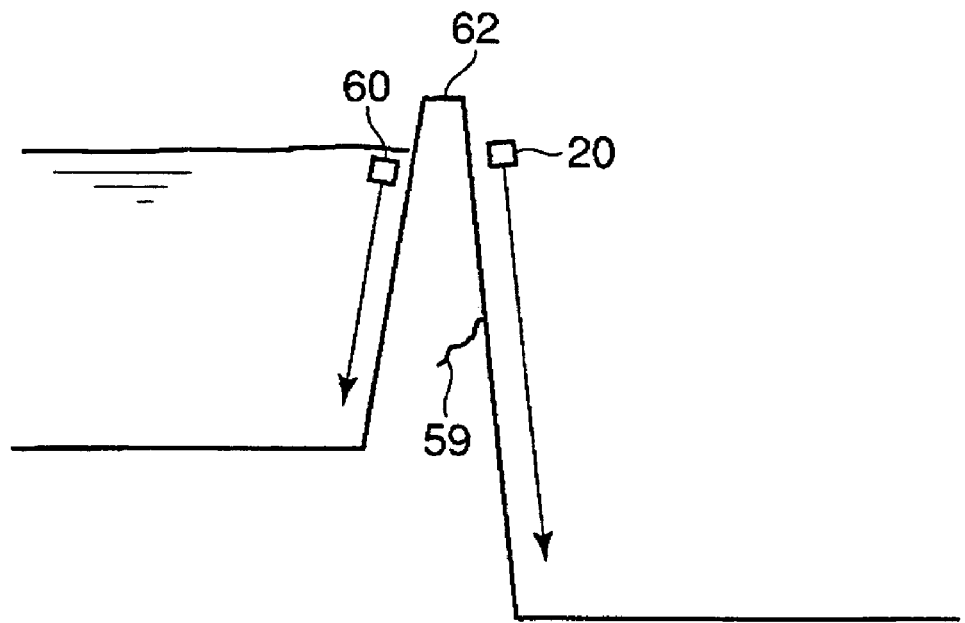
FIG. 15 is a schematic view for explaining a non-destructive test method of a dam according to the present sensor system.

FIG. 15 is a schematic view for explaining a non-destructive test method of a dam according to the present sensor system. As shown there, a case where a crack 59 exists in a dam wall 62 that ponds a river or stream is considered.

In this state, the hard X-ray source 60 and the sensor 20, while being opposed to each other with the dam wall 62 being interposed therebetween, are moved so as to cover all surfaces of the dam wall 62, so that the hard X-rays transmitted through the dam wall 62 are detected at each of positions. At this time, the strength of the hard X-rays measured at least in the vicinity of the crack 59 is influenced by the density change due to the crack 59 to deviate from the strength of the hard X-rays measured at the position where no crack 59 exists. Hence, the existence of the crack 59 can be evaluated.

Also, the hard X-rays measured in the vicinity of the crack 59 has less attenuation as compared with the hard X-rays measured in other areas where no crack exists and the strength thereof becomes higher by that degree. Thus, by obtaining a two-dimensional or three-dimensional distribution of the hard X-rays having the less attenuation, an approximate size of the crack 59 can be quantitatively evaluated.

(Non-Destructive Test of Nuclear Reactor)

Figure 16:
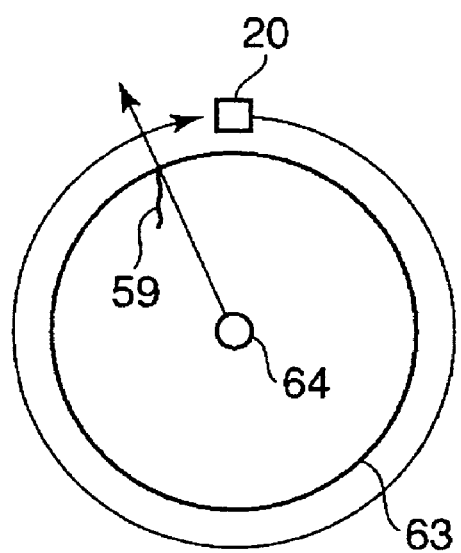
FIG. 16 is a schematic view for explaining a non-destructive test method of a nuclear reactor according to the present sensor system.

FIG. 16 is a schematic view (plan view) for explaining a non-destructive test method of a nuclear reactor 63 according to the present sensor system. As shown there, a case where a reactor core 64 exists in a central portion of a nuclear reactor 63 and a crack 59 exists in an outer wall of the nuclear reactor 63 is considered.

In this state, the sensor 20, while being opposed to the reactor core 64, is moved so as to cover all portions of the outer wall surface of the nuclear reactor 63, so that the hard X-rays are measured at each of positions. At this time, if there is no problem in the outer wall of the nuclear reactor 63, the sensor 20 detects no abnormality of the hard X-rays. But if the crack 59 exists in the outer wall of the nuclear reactor 63, a portion of the hard X-rays leaks from the crack 59. Hence, by detecting the hard X-rays by the sensor 20, the existence of the crack, etc. and the position thereof can be evaluated. Also, by obtaining a two-dimensional or three-dimensional distribution of the detected hard X-rays, an approximate size of the crack 59 can be quantitatively evaluated.

(Non-Destructive Test of Bridge, Tower, Etc.)

Figure 17:
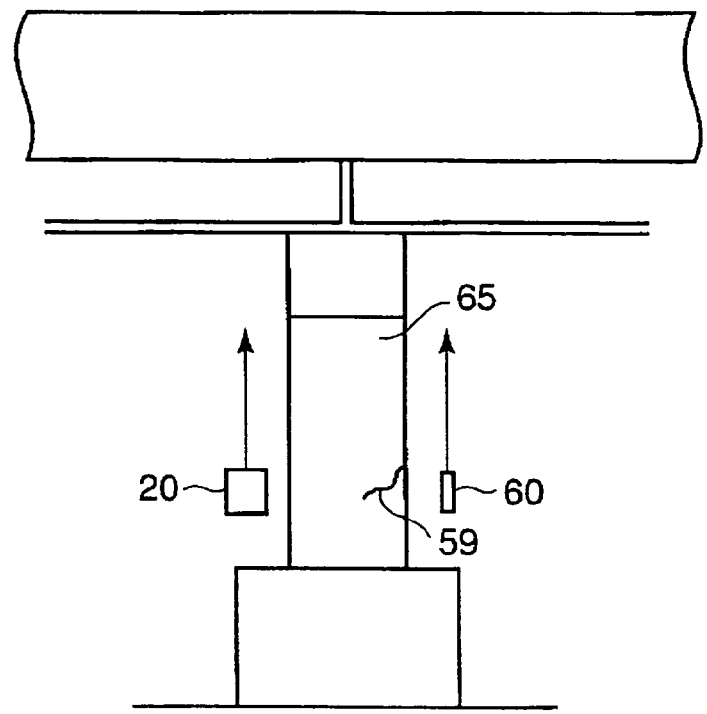
FIG. 17 is a schematic view for explaining a non-destructive test method of a bridge according to the present sensor system.
Figure 18:
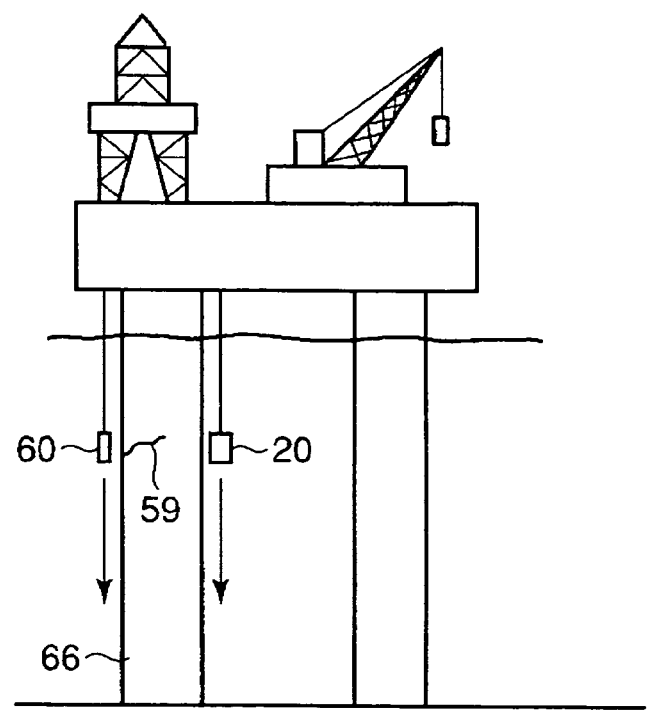
FIG. 18 is a schematic view for explaining a non-destructive test method of a tower (a platform used for development of an undersea oil field) according to the present sensor system.

FIG. 17 is a schematic view for explaining a non-destructive test method of a bridge 65 according to the present sensor system. Also, FIG. 18 is a schematic view for explaining a non-destructive test method of a tower (i.e., a platform used for development of an undersea oil field) 66 according to the present sensor system.

For each of these buildings, the non-destructive test can be carried out by the same method as in the case of the above-mentioned dam and nuclear reactor.

(Non-Destructive Test of Tunnel)

Figure 19:
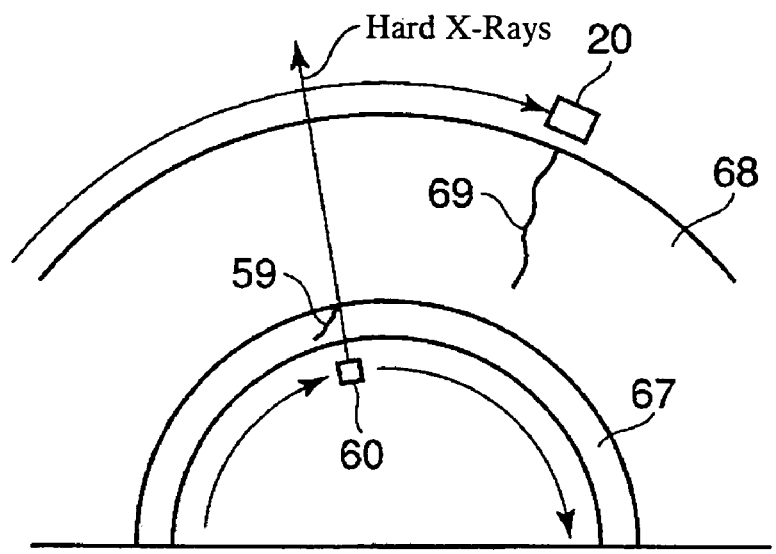
FIG. 19 is a schematic view for explaining a non-destructive test method of a tunnel wall according to the present sensor system.

FIG. 19 is a schematic view for explaining a non-destructive test method of a tunnel wall 67 according to the present sensor system. As shown there, a case where a crack 59 exists in a portion of the tunnel wall 67 is considered.

In this state, the hard X-ray source 60 and the sensor 20 are opposed to each other with the tunnel wall 67 and a stratum 68 being interposed therebetween and are moved so as to cover all surface portions of the tunnel wall 67 and the stratum 68, so that the transmitted hard X-rays are detected at each of positions. At this time, the strength of the hard X-rays measured at least in the vicinity of the crack 59 is influenced by the density change due to the crack 59 to deviate from the strength of the hard X-rays measured at the position where no crack 59 exists. Hence, the existence, etc. of the crack 59 can be evaluated.

Also, if a fault 69 exists, the strength of the transmitted hard X-rays is influenced also by the fault 69. Hence, by the degree of attenuation of the strength measured of the hard X-rays, the existence, position and size of the fault 69 in the stratum can be quantitatively evaluated.

According to the present method, a position and size not only of the fault but also of an active fault can be quantitatively evaluated. Moreover, by periodically evaluating the position, size, etc. of the active fault with a predetermined time interval, movement of that active fault also can be evaluated.

(Non-Destructive Test of Interior of Vessel or Piping)

Figure 20:
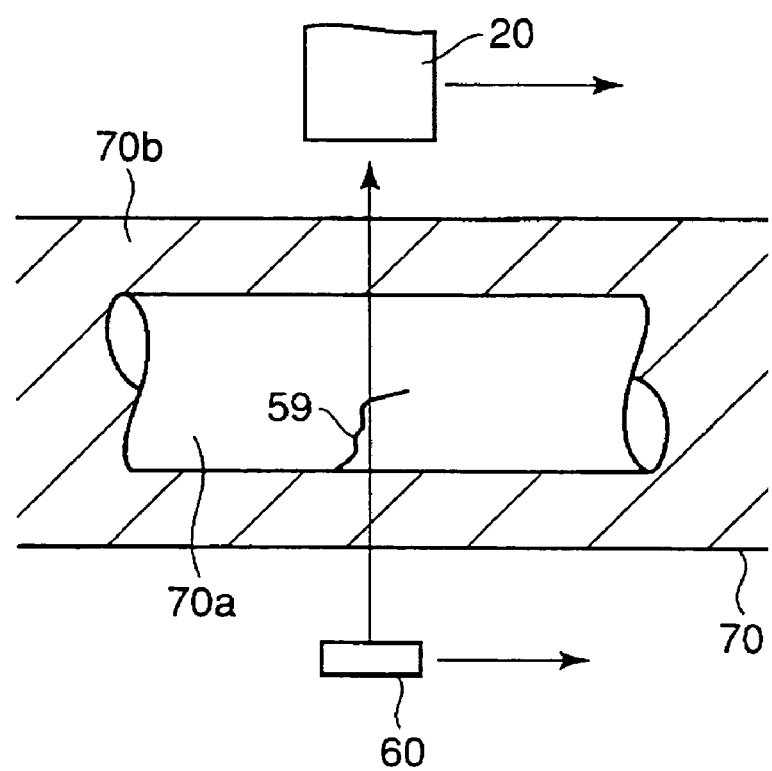
FIG. 20 is a schematic view for explaining a non-destructive test method of a vessel or piping according to the present sensor system.

FIG. 20 is a schematic view for explaining a non-destructive test method of an interior of a vessel or piping according to the present sensor system. As shown, a piping device 70 comprises a piping 70a and a heat insulating material 70b (for high temperature or low temperature).

In this state, supposing that a crack 59 exists in a portion of the piping 70a, for example, the hard X-ray source 60 and the sensor 20, while being opposed to each other with the piping 70a being interposed therebetween, are moved so as to cover all portions of an outer surface of the piping device 70, so that the transmitted hard X-rays are detected at each of positions. At this time, the strength of the hard X-rays measured at least in the vicinity of the crack 59 is influenced by the density change due to the crack 59. Hence, by analyzing the occurrence and the position thereof of the strength change of the hard X-rays caused by the density change as well as by analyzing a two-dimensional or three-dimensional distribution of the strength change, the existence, position and size of the crack 59 can be quantitatively evaluated.

Also, according to the present sensor system, thickness of the piping 70a can be measured. That is, the hard X-rays transmitted through the piping 70a are influenced by the thickness of the piping existing at the place of the transmittance so that the attenuation of the hard X-rays changes. For example, the hard X-rays transmitted through the piping having a larger thickness has a larger attenuation as compared with the hard X-rays transmitted through the piping having a smaller thickness. Hence, by analyzing the distribution of the degree of the attenuation, the distribution of the thickness of the piping can be grasped.

Moreover, if the material of the piping 70a is known, a concrete thickness of the piping can be obtained according to the degree of the attenuation. That is, the value of the deviation of the hard X-ray strength depends on the thickness of the piping. Hence, by comparing the deviation value using a table showing the relation between the transmission distance (thickness) and the hard X-ray strength, prepared for the substance constituting the piping, the thickness of the piping can be quantitatively evaluated.

(Non-Destructive Test of Ship, Etc.)

Figure 21:
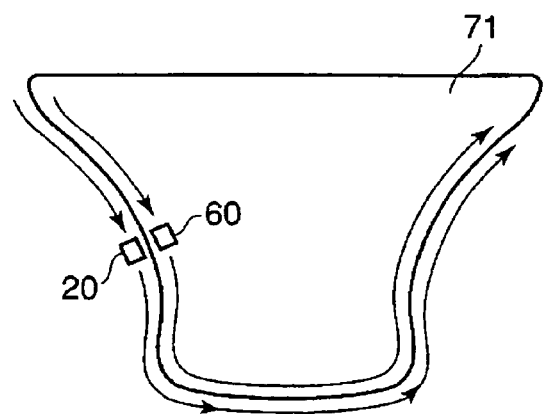
FIG. 21 is a schematic view for explaining a non-destructive test method of a ship according to the present sensor system.

FIG. 21 is a schematic view for explaining a non-destructive test method of a ship according to the present sensor system. As shown there, the hard X-ray source 60 and the sensor 20 are opposed to each other with a hull 71 being interposed therebetween and are moved so as to cover all portions of the hull 71, so that the hard X-rays are detected at each of positions. Thus, by detecting and analyzing the strength of the transmitted hard X-rays that has been influenced by the density change due to the crack 59, the existence, position and size of the crack 59 can be quantitatively evaluated.

(Fluid Analysis of Fluid in Vessel)

Next, an example where the above-mentioned sensor system is applied to a fluid analysis of fluid in a vessel will be described. This fluid analysis uses the evaluating method of the transmission wave detecting type and the state of fluid flow in the vessel can be grasped without need of opening or closing the vessel.

Figure 22:
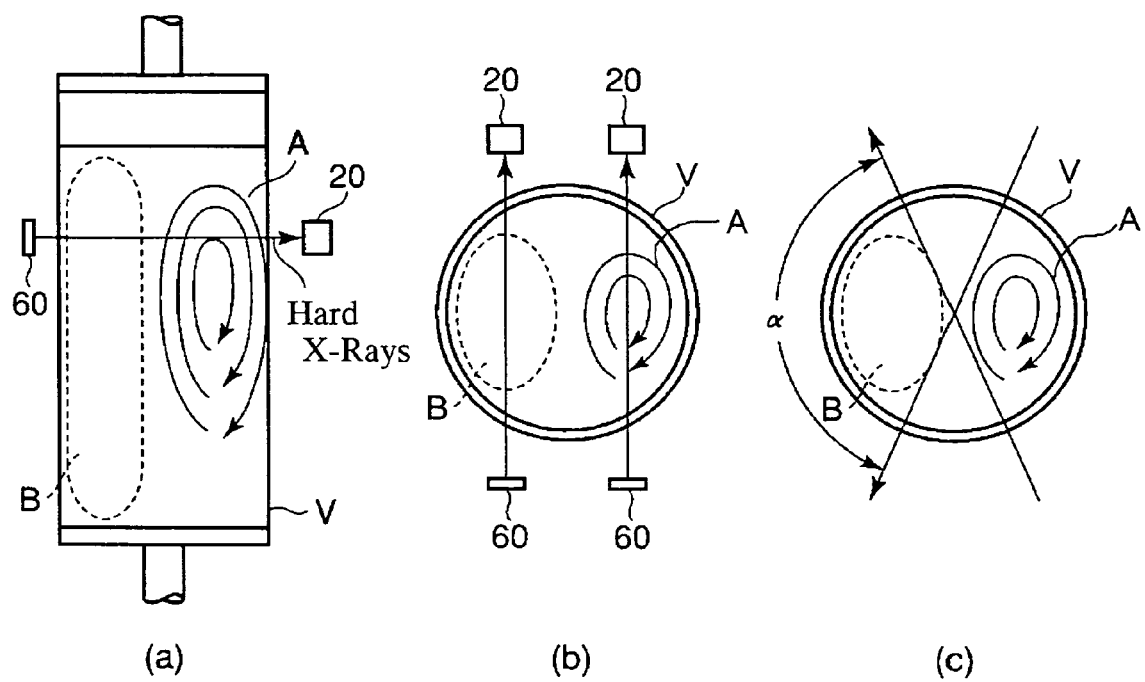
FIG. 22 includes FIGS. 22(a), 22(b) and 22(c), all for explaining a fluid analyzing method of fluid in a vessel according to the present sensor system.

FIGS. 22(a) to 22(e) are schematic views for explaining a fluid analyzing method of fluid in a vessel according to the present sensor system. As shown in FIG. 22(a), a case where there are an area A having a convection and an area B having no convection (no movement) in a vessel V is considered. As one reason for this state where there is caused no uniform convection in one vessel, it is considered that the density in the area B is higher than that in the area A.

In this state, the hard X-ray source 60 and the sensor 20 are arranged being opposed to each other with the vessel V being interposed therebetween and are moved so as to cover all portions of a side surface of the vessel V, so that the strength of the transmitted hard X-rays is measured at each of positions. In this case, as shown in FIG. 22(b), there arises a difference of the X-ray strength between the hard X-rays transmitted through the area B and the hard X-rays transmitted through the area A. Hence, by investigating the generation of the strength difference and a distribution of the hard X-ray transmission areas where the strength difference is generated, the convection state of the fluid in the vessel or the area where the convection arises can be evaluated.

While one example has been shown in FIG. 22(b), the mode of taking the transmission area of the hard X-rays (e.g., the mode of moving the mutually opposed hard X-ray source 60 and sensor 20) can be arbitrarily selected. For example, as shown in FIG. 22(c), if the transmission area of the hard X-rays is taken so that a line connecting the hard X-ray source 60 and the sensor 20 always passes through the center of the vessel of a cylindrical shape, the strength of the transmitted hard X-rays will be reduced specifically in the range of a rotational angle α. Hence, by further investigating a change of the transmitted hard X-ray strength in the length-wise direction of the cylindrical vessel V, the area where the convection is generated can be evaluated. It is to be noted that the mode of taking the transmission area of the hard X-rays corresponds to the mode of taking a coordinate system that specifies positions in the vessel. For example, the case of FIG. 22(b) corresponds to setting an orthogonal coordinate system in a column and the case of FIG. 22(c) corresponds to setting a columnar coordinate system in a column.

(Evaluating Method of Movement of Volcanic Magma)

Next, an example where the above-mentioned sensor system is applied to an evaluation of movement of volcanic magma will be described. This evaluation can be realized by the evaluation method either of the transmission wave detecting type or the reaction spectrum detecting type.

Figure 23:
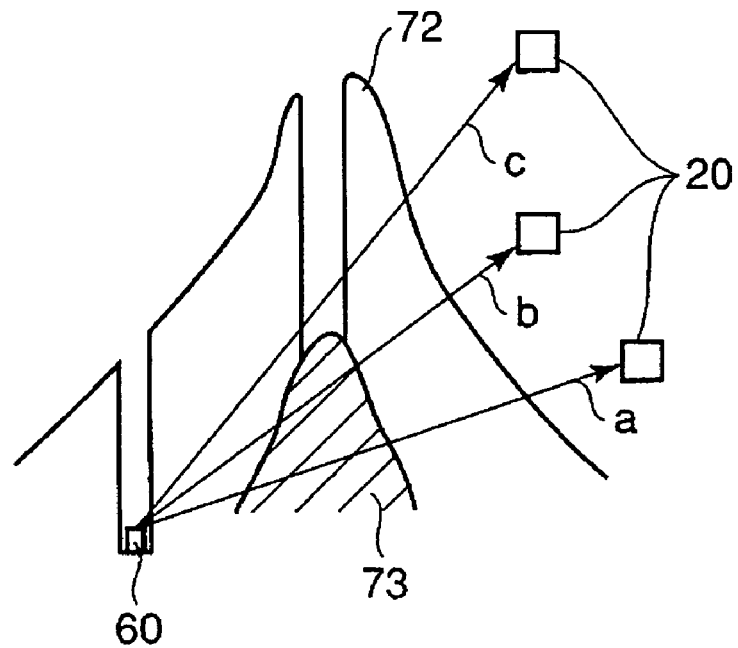
FIG. 23 is a schematic view for explaining a transmission wave detecting type evaluating method of a movement of volcanic magma according to the present sensor system.

The evaluation method of the transmission wave detecting type will be first described. FIG. 23 is a schematic view for explaining the evaluation of movement of volcanic magma of the transmission wave detecting type according to the present sensor system. As shown there, a well is bored in a portion of the skirts of a volcano 72 and the hard X-ray source 60 comprising cobalt 60, etc., for example, is arranged therein. Also, the sensor 20 is arranged on the opposite side thereof of the volcano 72 so as to detect the hard X-rays radiated from the hard X-ray source 60.

In this state, there is caused a difference of the hard X-ray strength between the hard X-rays a and b which are transmitted through magma 73 to be detected by the sensor 20 and the hard X-rays c not transmitted through the magma 73. That is, as compared with the hard X-rays c not transmitted through the magma 73, the hard X-rays a and b which are transmitted through the magma 73 are influenced by the transmission through the magma 73 that has a density (components) different from the surrounding stratum and there arises the difference in the strength. Hence, by investigating the generation of the strength difference and a distribution of the hard X-ray transmission areas where the strength difference is generated, a possibility of eruption of the magma 73 or an area where the magma 73 exists can be evaluated.

Figure 24:
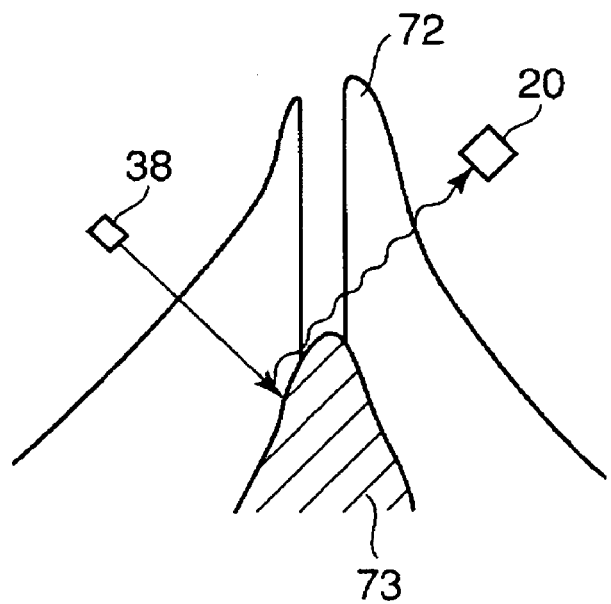
FIG. 24 is a schematic view for explaining a reaction spectrum detecting type evaluating method of a movement of volcanic magma according to the present sensor system.

Next, the evaluation method of the reaction spectrum detecting type will be described. FIG. 24 is a schematic view for explaining the evaluation of movement of volcanic magma of the reaction spectrum detecting type according to the present sensor system. As shown there, neutron is radiated by a neutron generator gun 38 toward an area including a magma path of the volcano 72. In this case, the radiated neutron is propagated in the magma 73 or reacts on (interacts with) a specific element constituting the magma 73.

Upon occurrence of such reaction, there arises a transition of the energy level of a particle (i.e., a nucleon of a predetermined atom) constituting the magma that has interacted with the neutron and hard X-rays having a spectrum proper to the element are generated. Hence, by measuring this spectrum by the sensor 20 and analyzing it, whether the magma exists or not in the area to which the neutron is radiated can be evaluated. Also, by measuring the strength (frequency of the generation) of the hard X-rays including the predetermined spectrum, the size of the magma 73 can be quantitatively evaluated.

[Evaluation of Buried Object (Ruins, Etc.)]

Next, an example where the above-mentioned sensor system is applied to an evaluation of whether ruins, etc. or a buried object hidden underground exists or not in a predetermined area will be described. This evaluation can be realized by the evaluation method either of the transmission wave detecting type or the reaction spectrum detecting type.

Figure 25:
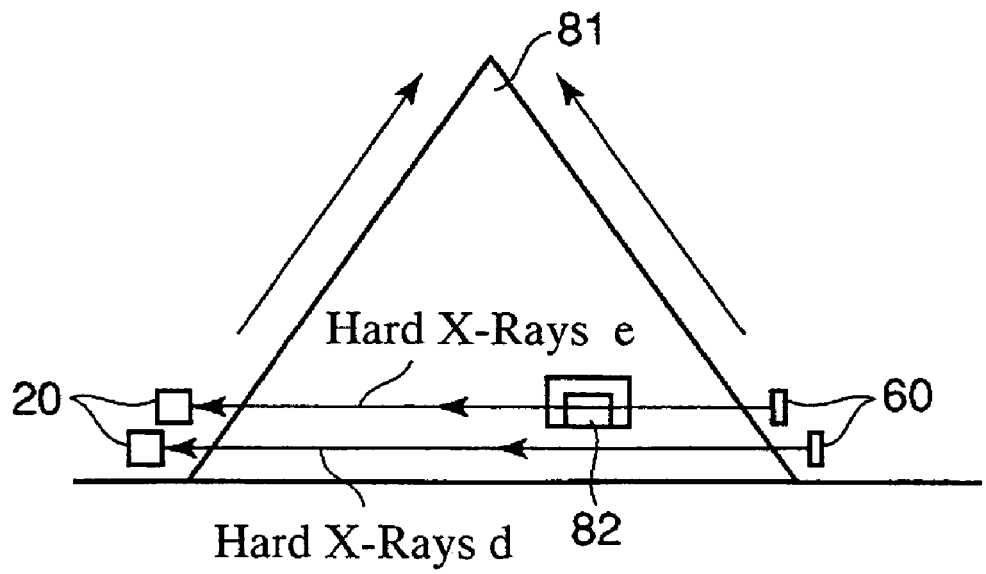
FIG. 25 is a schematic view for explaining a transmission wave detecting type evaluating method of a buried object in a building according to the present sensor system.

The evaluation method of the transmission wave detecting type will be first described. FIG. 25 is a schematic view for explaining the evaluation of the transmission wave detecting type of a buried object in a building according to the present sensor system. As shown there, the hard X-ray source 60 and the sensor 20 are arranged being opposed to each other with a ruins building 81 being interposed therebetween and are moved so as to cover all portions of side surface areas of the ruins building 81, so that that the transmitted hard X-rays are measured at each of positions.

In the hard X-rays so measured, there is caused a difference of the strength between the hard X-rays transmitted through a buried object 82 and the hard X-rays not transmitted through the buried object 82. That is, for example, a case where the buried object 82 is constituted by gold (Au) and the ruins building 81 is constituted by stone is considered. In this case, as compared with hard X-rays d transmitted through the ruins building 81 only, hard X-rays e transmitted through the buried object 82 are influenced by a density change of the propagation mediums due to the buried object 82 so that the attenuation of the strength is largely changed. Hence, by investigating the generation of the strength attenuation and a distribution of the transmission areas of the hard X-rays where the strength attenuation is generated, the existence of the buried object 82 and the existing area can be evaluated.

Figure 26:
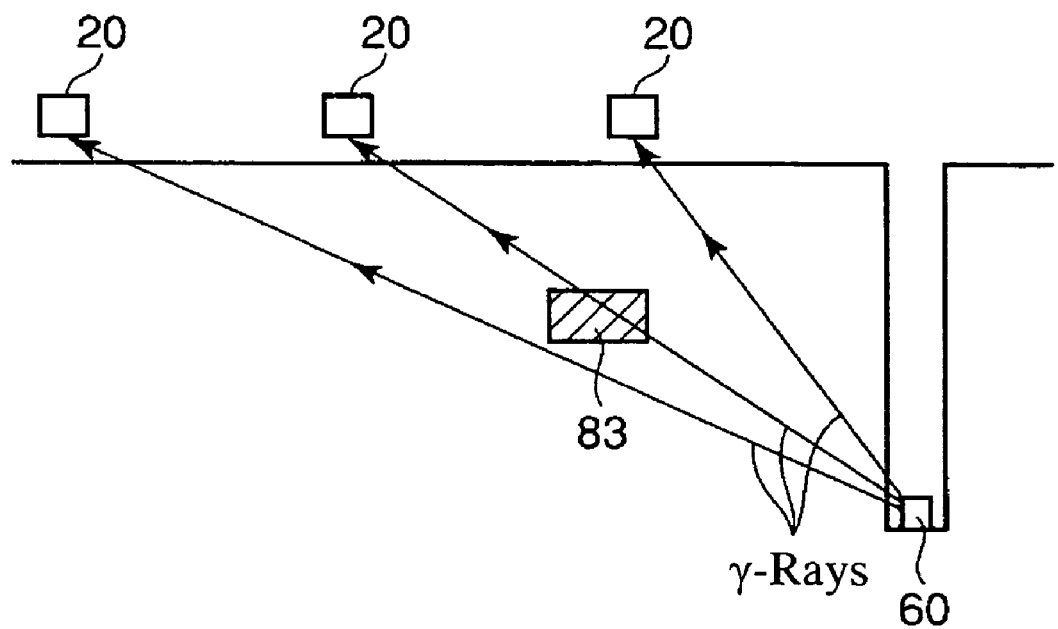
FIG. 26 is a schematic view for explaining a transmission wave detecting type evaluating method of a buried object buried underground according to the present sensor system.

FIG. 26 is a schematic view for explaining the evaluation of the transmission wave detecting type of a buried object 83 buried underground. As shown there, a well having a predetermined depth is bored and the hard X-ray source 60 is arranged therein. The hard X-rays radiated from the hard X-ray source 60 are measured by the sensor 20 at each of positions. Thereby, the same effect can be obtained.

With respect to the evaluation of the reaction spectrum detecting type also, the evaluation can be realized by the same method as the evaluation of movement of the volcanic magma, for example.

(Application to Medical Imaging Diagnosis)

The present sensor system can be applied to the field of a medical imaging diagnosis. Here, specifically, an application to a nuclear medicine diagnosing device will be described in which a medicine marked by a radioisotope element is injected into the human body as a diagnosis object and the radiation (γ-rays) radiated from the medicine that has gathered in a diseased part is detected from outside of the human body to be imaged.

In a prior art nuclear medicine diagnosing device, a scintillation camera is provided as a detector detecting the γ-rays and by secondarily performing a concurrent detection of the radiation radiated from the human body, an image is formed. Generally, a camera of a wide view using a monocrystal Na I scintillator (Anger's camera developed by Anger of USA) is mainly used.

In place of this scintillation camera, the present sensor system can be used. In this case, a detecting face of the present sensor is made as an image sensor in which a detecting element is formed in a two-dimensional matrix shape by a hole type electrode and a semi-conductor (CdTe, for example) as shown in FIG. 3. By this construction, a direct measurement of the γ-rays becomes possible and a nuclear medicine diagnosing device by which photographing having a higher resolution and wider field of view is possible can be realized.

(Application to Discovery of Military Weapons)

The present sensor system can be applied to a discovery of a place in the ground or in a building where military weapons are hidden. That is, for example, in FIG. 26, it is supposed that a buried object 83 buried in the ground is a mine or nuclear weapon or other military weapons. Even in such a case, by the same method as the evaluation of the above-described buried objects, the existence, position, size, etc. of the military weapons can be quantitatively evaluated.

(Use as Monitoring Camera)

The present sensor system can be used as a monitoring camera. For example, if an intruder gets under cover in a concrete building, the hard X-ray source and the sensor are arranged being opposed to each other with the building and the intruder being arranged therebetween and the hard X-rays transmitted through the building are detected. In the obtained hard X-rays, there is a difference of the strength between the hard X-rays transmitted through the area where the intruder exists and the hard X-rays not transmitted through the same area. Hence, by evaluating the quantity and area of the change, the existence of the intruder in an area where no infrared camera, etc. can be used is evaluated and the interior of the building can be monitored.

Also, by continuously performing this monitoring, movement of the intruder can be grasped. Moreover, by obtaining hard X-ray transmission data in the angular range of 360° around an outer periphery of the building and by performing an image re-construction processing, a more concrete structure and state of an interior of the building can be grasped.

In the above, while the technological concept of the present invention has been described based on each of the embodiments, the present invention is not limited to the embodiments but may be added with various modifications in the constructional elements within the scope of the appended claims. Also, by appropriately combining the plurality of constructional elements disclosed by the embodiments, various inventions can be formed. For example, some of the constructional elements may be deleted from the entire constructional elements shown in the embodiments. Or, some constructional elements included in the different embodiments may be appropriately combined.

What is claimed is:

1. An underground resource evaluating method comprising:
   arranging a radiation detector and an opposing radiation source radiating a first radiation of hard X-rays or γ-rays such that at least a portion of an underground resource to be evaluated is interposed between the radiation detector and the radiation source;
   detecting a second radiation transmitted from the radiation source, the second radiation being a portion of the first radiation which is transmitted from the radiation source through a portion of the underground resource to be evaluated; and
   evaluating a strength of the second radiation detected by said detecting of the second radiation and a strength of the first radiation so as to determine a presence of the underground resource.

2. The underground resource evaluating method as claimed in claim 1, wherein:
   the underground resource is crude oil; and
   said evaluating of the strength includes estimating an existence of an oil field based on a strength relative to a propagation distance of the first radiation in the crude oil and the strength of the second radiation.

3. The underground resource evaluating method as claimed in claim 2, further comprising detecting a third radiation from the radiation source, the third radiation being a portion of the first radiation which has not been transmitted through any portion of the underground resource, wherein:
   said detecting of the second radiation includes detecting the second radiation from a plurality of different locations; and
   said evaluating of the strength includes:
      estimating a propagation distance of the second radiation in the underground resource for at least one of the plurality of different locations from which the second radiation is detected by said detecting of the second radiation, based on a strength relative to a propagation distance of the first radiation and the strength of the second radiation; and
      quantitatively evaluating the underground resource based on at least one of the propagation distances of the second radiation estimated by said estimating of the propagation distance and a detection distribution representing a distribution of the second radiation detected from the plurality of different locations.

4. The underground resource evaluating method as claimed in claim 1, wherein:
   the underground resource is natural gas; and
   said evaluating of the strength includes estimating an existence of a natural gas field based on a strength relative to a propagation distance of the first radiation in the natural gas and the strength of the second radiation.

5. The underground resource evaluating method as claimed in claim 4, further comprising detecting a third radiation from the radiation source, the third radiation being a portion of the first radiation which has not been transmitted through any portion of the underground resource, wherein:
   said detecting of the second radiation includes detecting the second radiation from a plurality of different locations; and
   said evaluating of the strength includes:
      estimating a propagation distance of the second radiation in the underground resource for at least one of the plurality of different locations from which the second radiation is detected by said detecting of the second radiation, based on a strength relative to a propagation distance of the first radiation and the strength of the second radiation; and quantitatively evaluating the underground resource based on at least one of the propagation distances of the second radiation estimated by said estimating of the propagation distance and a detection distribution representing a distribution of the second radiation detected from the plurality of different locations.

6. The underground resource evaluating method as claimed in claim 1, wherein:

the underground resource is coal; and said evaluating of the strength includes estimating an existence of a coal field based on a strength relative to a propagation distance of the first radiation in the coal and the strength of the second radiation.

7. The underground resource evaluating method as claimed in claim 6, further comprising detecting a third radiation from the radiation source, the third radiation being a portion of the first radiation which has not been transmitted through any portion of the underground resource, wherein:

said detecting of the second radiation includes detecting the second radiation from a plurality of different locations; and said evaluating of the strength includes:

estimating a propagation distance of the second radiation in the underground resource for at least one of the plurality of different locations from which the second radiation is detected by said detecting of the second radiation, based on a strength relative to a propagation distance of the first radiation and the strength of the second radiation; and quantitatively evaluating the underground resource based on at least one of the propagation distances of the second radiation estimated by said estimating of the propagation distance and a detection distribution representing a distribution of the second radiation detected from the plurality of different locations.

8. The underground resource evaluating method as claimed in claim 1, wherein:

the underground resource is a predetermined metal; and said evaluating of the strength includes estimating an existence of an ore deposit of the predetermined metal based on a strength relative to a propagation distance of the first radiation in the predetermined metal and the strength of the second radiation.

9. The underground resource evaluating method as claimed in claim 8, further comprising detecting a third radiation from the radiation source, the third radiation being a portion of the first radiation which has not been transmitted through any portion of the underground resource, wherein:

said detecting of the second radiation includes detecting the second radiation from a plurality of different locations; and said evaluating of the strength includes:

estimating a propagation distance of the second radiation in the underground resource for at least one of the plurality of different locations from which the second radiation is detected by said detecting of the second radiation, based on a strength relative to a propagation distance of the first radiation and the strength of the second radiation; and quantitatively evaluating the underground resource based on at least one of the propagation distances of the second radiation estimated by said estimating of the propagation distance and a detection distribution representing a distribution of the second radiation detected from the plurality of different locations.

10. The underground resource evaluating method as claimed in claim 1, further comprising detecting a third radiation from the radiation source, the third radiation being a portion of the first radiation which has not been transmitted through any portion of the underground resource, wherein:

said detecting of the second radiation includes detecting the second radiation from a plurality of different locations; and said evaluating of the strength includes:

estimating a propagation distance of the second radiation in the underground resource for at least one of the plurality of different locations from which the second radiation is detected by said detecting of the second radiation, based on a strength relative to a propagation distance of the first radiation and the strength of the second radiation; and quantitatively evaluating the underground resource based on at least one of the propagation distances of the second radiation estimated by said estimating of the propagation distance and a detection distribution representing a distribution of the second radiation detected from the plurality of different locations.

11. An underground waste evaluating method comprising:

arranging a radiation detector and an opposing radiation source radiating a first radiation of hard X-rays or γ-rays such that at least a portion of underground waste to be evaluated is interposed between the radiation detector and the radiation source;

detecting a second radiation transmitted from the radiation source, the second radiation being a portion of the first radiation which is transmitted from the radiation source through a portion of the underground waste to be evaluated; and evaluating a strength of the second radiation detected by said detecting of the second radiation and a strength of the first radiation so as to determine a presence of the underground waste.

12. The underground waste evaluating method as claimed in claim 11, wherein:

the underground waste is an injected carbon dioxide; and said evaluating of the strength includes estimating an existence of the injected carbon dioxide based on a strength relative to a propagation distance of the first radiation in the injected carbon dioxide and the strength of the second radiation.

13. The underground waste evaluating method as claimed in claim 12, further comprising detecting a third radiation from the radiation source, the third radiation being a portion of the first radiation which has not been transmitted through any portion of the underground waste, wherein:

said detecting of the second radiation includes detecting the second radiation from a plurality of different locations; and said evaluating of the strength includes:

estimating a propagation distance of the second radiation in the underground waste for at least one of the plurality of different locations from which the second radiation is detected by said detecting of the second radiation, based on a strength relative to a propagation distance of the first radiation and the strength of the second radiation; and quantitatively evaluating the underground waste based on at least one of the propagation distances of the second radiation estimated by said estimating of the propagation distance and a detection distribution representing a distribution of the second radiation detected from the plurality of different locations.

14. The underground waste evaluating method as claimed in claim 11, further comprising detecting a third radiation from the radiation source, the third radiation being a portion of the first radiation which has not been transmitted through any portion of the underground waste, wherein:

said detecting of the second radiation includes detecting the second radiation from a plurality of different locations; and said evaluating of the strength includes:

estimating a propagation distance of the second radiation in the underground waste for at least one of the plurality of different locations from which the second radiation is detected by said detecting of the second radiation, based on a strength relative to a propagation distance of the first radiation and the strength of the second radiation; and quantitatively evaluating the underground waste based on at least one of the propagation distances of the second radiation estimated by said estimating of the propagation distance and a detection distribution representing a distribution of the second radiation detected from the plurality of different locations.

15. An underground preserved object evaluating method comprising:

arranging a radiation detector and an opposing radiation source radiating a first radiation of hard X-rays or γ-rays such that at least a portion of an underground preserved object is interposed between the radiation detector and the radiation source;

detecting a second radiation transmitted from the radiation source, the second radiation being a portion of the first radiation which is transmitted from the radiation source through a portion of the underground preserved object; and evaluating a strength of the second radiation detected by said detecting of the second radiation and a strength of the first radiation so as to determine a presence of the underground preserved object.

16. The underground preserved object evaluating method as claimed in claim 15, wherein:

the underground preserved object is natural gas; and said evaluating of the strength includes estimating an existence of the natural gas based on a strength relative to a propagation distance of the first radiation in the natural gas and the strength of the second radiation.

17. The underground preserved object evaluating method as claimed in claim 16, further comprising detecting a third radiation from the radiation source, the third radiation source being a portion of the first radiation which has not been transmitted through any portion of the underground preserved object, wherein:

said detecting of the second radiation includes detecting the second radiation from a plurality of different locations; and said evaluating of the strength includes:

estimating a propagation distance of the second radiation in the underground preserved object for at least one of the plurality of different locations from which the second radiation is detected by said detecting of the second radiation, based on a strength relative to a propagation distance of the first radiation and the strength of the second radiation; and quantitatively evaluating the underground preserved object based on at least one of the propagation distances of the second radiation estimated by said estimating of the propagation distance and a detection distribution representing a distribution of the second radiation detected from the plurality of different locations.

18. The underground preserved object evaluating method as claimed in claim 15, further comprising detecting a third radiation from the radiation source, the third radiation source being a portion of the first radiation which has not been transmitted through any portion of the underground preserved object, wherein:

said detecting of the second radiation includes detecting the second radiation from a plurality of different locations; and said evaluating of the strength includes:

estimating a propagation distance of the second radiation in the underground preserved object for at least one of the plurality of different locations from which the second radiation is detected by said detecting of the second radiation, based on a strength relative to a propagation distance of the first radiation and the strength of the second radiation; and quantitatively evaluating the underground preserved object based on at least one of the propagation distances of the second radiation estimated by said estimating of the propagation distance and a detection distribution representing a distribution of the second radiation detected from the plurality of different locations.

19. An underground buried object evaluating method comprising:

arranging a radiation detector and an opposing radiation source radiating a first radiation of hard X-rays or γ-rays such that at least a portion of an underground buried object to be evaluated is interposed between the radiation detector and the radiation source;

detecting a second radiation transmitted from the radiation source, the second radiation being a portion of the first radiation which is transmitted from the radiation source through a portion of the underground buried object; and evaluating a strength of the second radiation detected by said detecting of the second radiation and a strength of the first radiation so as to determine a presence of the underground buried object.

20. The underground buried object evaluating method as claimed in claim 19, wherein:

the underground buried object is a mine, nuclear weapon or other military weapon, or any other buried object; and said evaluating of the strength includes estimating an existence of the mine, nuclear weapon or other military weapon, or any other buried object based on a strength relative to a propagation distance of the first radiation in the mine, nuclear weapon or other military weapon, or any other buried object and the strength of the second radiation.

21. The underground buried object evaluating method as claimed in claim 20, further comprising detecting a third radiation from the radiation source, the third radiation source being a portion of the first radiation which has not been transmitted through any portion of the underground buried object, wherein:

said detecting of the second radiation includes detecting the second radiation from a plurality of different locations; and said evaluating of the strength includes:

estimating a propagation distance of the second radiation in the underground buried object for at least one of the plurality of different locations from which the second radiation is detected by said detecting of the second radiation, based on a strength relative to a propagation distance of the first radiation and the strength of the second radiation; and quantitatively evaluating the underground buried object based on at least one of the propagation distances of the second radiation estimated by said estimating of the propagation distance and a detection distribution representing a distribution of the second radiation detected from the plurality of different locations.

22. The underground buried object evaluating method as claimed in claim 19, further comprising detecting a third radiation from the radiation source, the third radiation source being a portion of the first radiation which has not been transmitted through any portion of the underground buried object, wherein:

said detecting of the second radiation includes detecting the second radiation from a plurality of different locations; and said evaluating of the strength includes:
estimating a propagation distance of the second radiation in the underground buried object for at least one of the plurality of different locations from which the second radiation is detected by said detecting of the second radiation, based on a strength relative to a propagation distance of the first radiation and the strength of the second radiation; and quantitatively evaluating the underground buried object based on at least one of the propagation distances of the second radiation estimated by said estimating of the propagation distance and a detection distribution representing a distribution of the second radiation detected at from the plurality of different locations.

23. A volcanic activity evaluating method comprising:
arranging a radiation detector and an opposing radiation source radiating a first radiation of hard X-rays or γ-rays such that at least a portion of magma from a volcano to be evaluated is interposed between the radiation detector and the radiation source;

detecting a second radiation transmitted from the radiation source, the second radiation being a portion of the first radiation which is transmitted from the radiation source through a portion of the magma from the volcano; and evaluating a strength of the second radiation detected by said detecting of the second radiation and a strength of the first radiation so as to determine a presence of the magma from the volcano.

24. The volcanic activity evaluating method as claimed in claim 23, further comprising detecting a third radiation from the radiation source, the third radiation being a portion of the first radiation which has not been transmitted through any portion of the magma from the volcano, wherein:

said detecting of the second radiation includes detecting the second radiation from a plurality of different locations; and said evaluating of the strength includes:
estimating a propagation distance of the second radiation in the magma from the volcano for at least one of the plurality of different locations from which the second radiation is detected by said detecting of the second radiation, based on a strength relative to a propagation distance of the first radiation and the strength of the second radiation; and quantitatively evaluating the activity of the volcano based on at least one of the propagation distances of the second radiation estimated by said estimating of the propagation distance and a detection distribution representing a distribution of the second radiation detected from the plurality of different locations.

25. A stratum structure evaluating method comprising:
arranging a radiation detector and an opposing radiation source radiating a first radiation of hard X-rays or γ-rays such that a stratum structure is interposed between the radiation detector and the radiation source;

detecting a second radiation transmitted from the radiation source, the second radiation being a portion of the first radiation which is transmitted from the radiation source through the stratum structure; and evaluating a strength of the second radiation detected by said detecting of the second radiation and a strength of the first radiation so as to determine a presence of a fault or an active fault within the stratum structure.

26. The stratum structure evaluating method as claimed in claim 25, further comprising detecting a third radiation from the radiation source, the third radiation being a portion of the first radiation which has not been transmitted through the fault or the active fault within the stratum structure, wherein:

said detecting of the second radiation includes detecting the second radiation from a plurality of different locations; and said evaluating of the strength includes:
estimating a propagation distance of the second radiation in the fault or the active fault within the stratum structure for at least one of the plurality of different locations from which the second radiation is detected by said detecting of the second radiation, based on a strength relative to a propagation distance of the first radiation and the strength of the second radiation; and quantitatively evaluating the fault or the active fault based on at least one of the propagation distances of the second radiation estimated by said estimating of the propagation distance and a detection distribution representing a distribution of the second radiation detected from the plurality of different locations.

* * * * *